US008357807B2

(12) United States Patent
Naddaka et al.

(10) Patent No.: US 8,357,807 B2
(45) Date of Patent: *Jan. 22, 2013

(54) ISOQUINOLINIUM COMPOUNDS USEFUL IN THE PREPARATION OF CISATRACURIUM AND ASSOCIATED INTERMEDIATES

(75) Inventors: Vladimir Naddaka, Petach Tivka (IL); Shen Jingshan, Shanghai (CN); Oded Arad, Rehovot (IL); Guo Hongli, Shanghai (CN); Ofer Sharon, Petach Tikva (IL); Eyal Klopfer, Tel Aviv (IL); Shady Saeed, Haifa (IL)

(73) Assignee: CHEMAGIS Ltd., Bnei Brak (IL)

( * ) Notice: Subject to any disclaimer, the term of this patent is extended or adjusted under 35 U.S.C. 154(b) by 362 days.

This patent is subject to a terminal disclaimer.

(21) Appl. No.: 12/598,378

(22) PCT Filed: May 1, 2008

(86) PCT No.: PCT/IL2008/000586
§ 371 (c)(1),
(2), (4) Date: Mar. 4, 2010

(87) PCT Pub. No.: WO2008/132746
PCT Pub. Date: Nov. 6, 2008

(65) Prior Publication Data
US 2010/0168431 A1    Jul. 1, 2010

Related U.S. Application Data

(60) Provisional application No. 60/915,326, filed on May 1, 2007.

(51) Int. Cl.
*C07D 217/16* (2006.01)
(52) U.S. Cl. ........................................ 546/146; 546/147
(58) Field of Classification Search ........................ None
See application file for complete search history.

(56) References Cited

U.S. PATENT DOCUMENTS

| 4,179,507 | A | 12/1979 | Stenlake et al. |
| 4,491,665 | A | 1/1985 | El-Sayad et al. |
| 4,701,460 | A | 10/1987 | El-Sayad et al. |
| 4,761,418 | A | 8/1988 | Swaringen, Jr. et al. |
| 4,851,537 | A | 7/1989 | Noyori et al. |
| 4,988,815 | A | 1/1991 | Andre et al. |
| 5,240,939 | A | 8/1993 | Demko |
| 5,453,510 | A | 9/1995 | Hill et al. |
| 5,556,978 | A | 9/1996 | Hill et al. |
| 5,684,154 | A | 11/1997 | Chamber et al. |
| 6,015,903 | A | 1/2000 | Viergutz et al. |
| 6,177,445 | B1 | 1/2001 | Bigham et al. |
| 6,187,789 | B1 | 2/2001 | Bigham et al. |
| 6,830,933 | B2 | 12/2004 | Lemmens et al. |
| 7,265,099 | B1 | 9/2007 | Bom et al. |
| 2006/0009485 | A1 | 1/2006 | Friedman et al. |
| 2008/0139482 | A1 | 6/2008 | Savarese |
| 2009/0156562 | A1 | 6/2009 | Winch |
| 2010/0016596 | A1 | 1/2010 | Pozzoli et al. |
| 2010/0087650 | A1 | 4/2010 | Ostrovsky et al. |
| 2010/0099878 | A1 | 4/2010 | Arad et al. |
| 2010/0174082 | A1 | 7/2010 | Arad et al. |
| 2010/0184988 | A1 | 7/2010 | Naddaka et al. |
| 2010/0234602 | A1 | 9/2010 | Arad et al. |
| 2010/0256381 | A1 | 10/2010 | Arad et al. |
| 2010/0298570 | A1 | 11/2010 | Segnalini et al. |
| 2011/0185796 | A1 | 8/2011 | Arad et al. |

FOREIGN PATENT DOCUMENTS

| CN | 101084896 A | 12/2007 |
| CN | 101337935 A | 1/2009 |
| CN | 101337936 A | 1/2009 |
| CN | 101475530 A | 7/2009 |
| CN | 101845017 A | 9/2010 |
| EP | 0 219 616 | 4/1987 |
| EP | 0219616 | 4/1987 |
| WO | WO 92/00965 A1 | 1/1992 |
| WO | WO 98/42675 A1 | 10/1998 |
| WO | WO 2007/091753 A1 | 8/2007 |
| WO | WO 2008/107887 A2 | 9/2008 |
| WO | WO 2008/117271 A1 | 10/2008 |
| WO | WO 2008/132748 A1 | 11/2008 |
| WO | WO 2008/155752 A1 | 12/2008 |
| WO | WO 2009/007946 A1 | 1/2009 |
| WO | WO 2009/057086 A1 | 5/2009 |
| WO | WO 2009/106547 A1 | 9/2009 |
| WO | WO 2009/133556 A2 | 11/2009 |
| WO | WO 2010/128518 A2 | 11/2010 |
| WO | WO 2010/128519 A1 | 11/2010 |

OTHER PUBLICATIONS

Stenlake et al, European Journal of Medicinal Chemistry, vol. 18, No. 3, pp. 273-276, 1983.*
Lindon et al. "Directly coupled HPLC-NMR and HPLC-NMR-MS in pharmaceutical research and development," Journal of Chromatography B : Biomedical Applications, Elsevier Science Publishers, NL, vol. 748, No. 1, pp. 233-258 (Oct. 1, 2000).
Liu et al. "High-performance liquid chromatography of atracurium besylate," Yao Hsueh Hsueh Pao—Acta Pharmaceutica Sinica, Beijing, CN, vol. 29, No. 1, pp. 68-73 (Jan. 1, 1994).
Mistry et al. "Directly Coupled Chiral HPLC-NMR and HPLC-CD Spectroscopy as Complementary Methods for Structural and Enantiomeric Isomer Identification: Application to Atracurium Besylate," Analytical Chemistry, vol. 71, No. 14, pp. 2838-2843 (1999).
Nehmer "Separation of cis-cis, cis-trans and trans-trans isomers of (.+-.)-atracurium besylate and cis and trans isomers of its major quaternary decomposition products and related impurity by reversed-phase high-performance liquid chromatography," Journal of Chromatography, vol. 457, pp. 127-135 (1988).
Stenlake et al: "Biodegradable Neuromuscular Blocking Agents 6. Stereochemical Studies on Atracurium and Related Polyalkylene Diesters," European Journal of Medicinal Chemistry, Editions Scientifique Elsevier, Paris, FR, vol. 19, No. 5, pp. 441-450 (Jan. 1, 1984).
Stenlake et al., "Neuromuscular Block Agents: Some approaches to short acting compounds," European Journal of Medicinal Chemistry, vol. 27, No. 5, pp. 463-477 (1992).

(Continued)

*Primary Examiner* — Zinna Northington Davis
(74) *Attorney, Agent, or Firm* — Leydig, Voit & Mayer, Ltd.

(57) ABSTRACT

The present invention provides novel isoquinolinium compounds, methods of producing the isoquinolinium compounds, and methods for converting them into cisatracurium, e.g., cisatracurium besylate. The isoquinolinium compounds of the present invention can be obtained in the form of solids, which can be purified using simple techniques and can be used to afford pure cisatracurium besylate without HPLC purification.

22 Claims, 14 Drawing Sheets

OTHER PUBLICATIONS

ICH Guideline, International Conference on Harmonization of Technical Requirements of Registration of Pharmaceuticals for Human Use (ICH), ICH Q3CR4 residual solvents MEDIA5254 (Feb. 2009).

European Patent Office, International Search Report in International Patent Application No. PCT/IL2008/000291 (Jul. 4, 2008).

European Patent Office, International Search Report in International Patent Application No. PCT/IL2008/000290 (Jul. 7, 2008).

European Patent Office, International Search Report in International Patent Application No. PCT/IL2008/000289 (Sep. 5, 2008).

European Patent Office, International Search Report in International Patent Application No. PCT/IL2008/000586 (Aug. 27, 2008).

European Patent Office, International Search Report in International Patent Application No. PCT/IL2008/000589 (Aug. 21, 2008).

European Patent Office, International Search Report in International Patent Application No. PCT/IL2008/000590 (Aug. 29, 2008).

European Patent Office, International Search Report in International Patent Application No. PCT/IL2008/001329 (Feb. 4, 2009).

U.S. Patent & Trademark Office, International Search Report in International Patent Application No. PCT/IL2009/000452 (Aug. 12, 2009).

* cited by examiner

ISOQUINOLINIUM COMPOUNDS USEFUL IN THE PREPARATION OF CISATRACURIUM AND ASSOCIATED INTERMEDIATES

CROSS-REFERENCE TO RELATED APPLICATIONS

This patent application is the U.S. National Phase of International Patent Application No. PCT/IL2008/000586, filed May 1, 2008, which claims the benefit of U.S. Provisional Patent Application No. 60/915,326, filed May 1, 2007, which are incorporated herein by reference in their entirety.

TECHNICAL FIELD

The present invention relates to organic chemistry and more particularly to novel isoquinolinium compounds and their use in the preparation of cisatracurium compounds.

BACKGROUND OF THE INVENTION

Cisatracurium besylate has the chemical name (1R,1'R,2R,2'R)-2,2'-[1,5-pentanediylbis[oxy(3-oxo-3,1-propanediyl)]]bis[1-[(3,4-dimethoxyphenyl)methyl]-1,2,3,4-tetrahydro-6,7-dimethoxy-2-methyl-isoquinolinium dibenzenesulfonate and is represented by the structural formula (I) below:

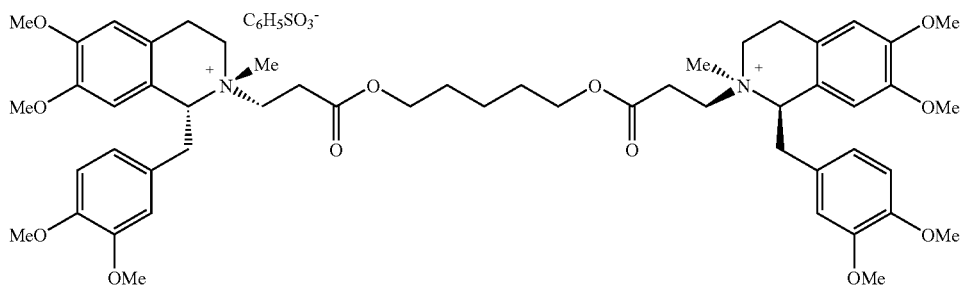

Cisatracurium besylate (I)

Cisatracurium besylate is the dibenzenesulfonate salt of 1R-cis,1'R-cis isomer of atracurium besylate. The atracurium compound has four chiral centers resulting in 16 possible isomers. Due to the symmetry of the molecule, the number of isomers is reduced to 10. The possible isomers of atracurium besylate are detailed by J. B. Stenlake et al. in "Biodegradable neuromuscular blocking agents", *Eur. J. Med. Chem.—Chem. Ther.*, vol. 19, issue 5, pp. 441-450 (1984).

Cisatracurium besylate is a nondepolarizing neuromuscular blocking agent indicated for inpatients and outpatients as an adjunct to general anesthesia, to facilitate tracheal intubation, and to provide skeletal muscle relaxation during surgery or mechanical ventilation in the Intensive Care Unit (ICU). Cisatracurium besylate possesses an activity that is superior to atracurium besylate, with significantly less side effects.

Cisatracurium besylate is marketed in the United States and Europe by Glaxo and Abbott Laboratories under the trade name Nimbex®.

Nimbex® is a sterile, non-pyrogenic aqueous solution that is adjusted to pH 3.25 to 3.65 with benzenesulfonic acid. The drug is provided in 2.5 ml, 5 ml and 10 ml ampules having a strength of 2 mg/ml cisatracurium besylate. In addition, a 30 ml vial containing 5 mg/ml cisatracurium besylate is also available.

Cisatracurium besylate slowly loses potency with time at a rate of approximately 5% per year under refrigeration (5° C.). Nimbex should be refrigerated at 2° to 8° C. (36° to 46° F.) in the carton to preserve potency. The rate of loss in potency increases to approximately 5% per month at 25° C. (77° F.).

Atracurium besylate, otherwise known as 2,2'-[1,5-pentanediylbis[oxy(3-oxo-3,1-propanediyl)]]bis[1-[(3,4-dimethoxyphenyl)methyl]-1,2,3,4-tetrahydro-6,7-dimethoxy-2-methyl-isoquinolinium dibenzenesulfonate, was first disclosed in U.S. Pat. No. 4,179,507 (hereinafter U.S. '507). U.S. '507 describes a series of bis veratryl isoquinolinium quaternary ammonium salts, preferably among them is atracurium besylate. The synthesis of atracurium besylate, as taught in U.S. '507, involves the coupling of (±)-tetrahydropapaverine base (compound II), with 1,5-pentamethylene diacrylate (compound III). Treatment of the resulting tertiary amine base with oxalic acid results in the isolation of N,N'-4,10-dioxa-3,11-dioxotridecylene-1,13-bis-tetrahydropapaverine dioxalate (compound IV). The dioxalate salt (compound IV) is converted to the free base (compound V), which is treated with methyl benzenesulfonate. The resulting product, atracurium besylate (compound VI), is precipitated and isolated. Scheme 1 below illustrates the chemical pathway described above.

Scheme 1

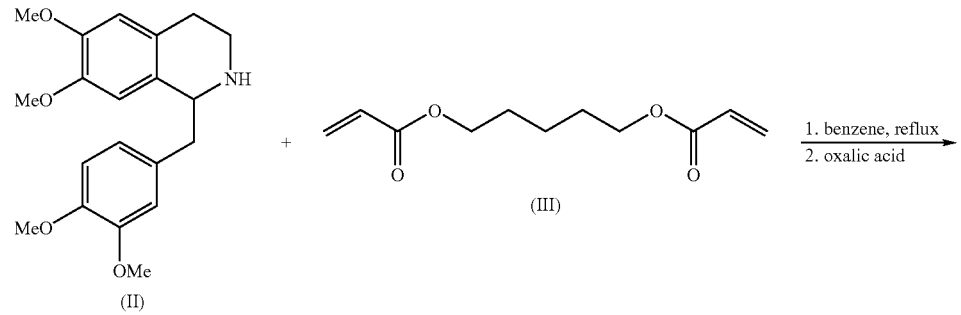

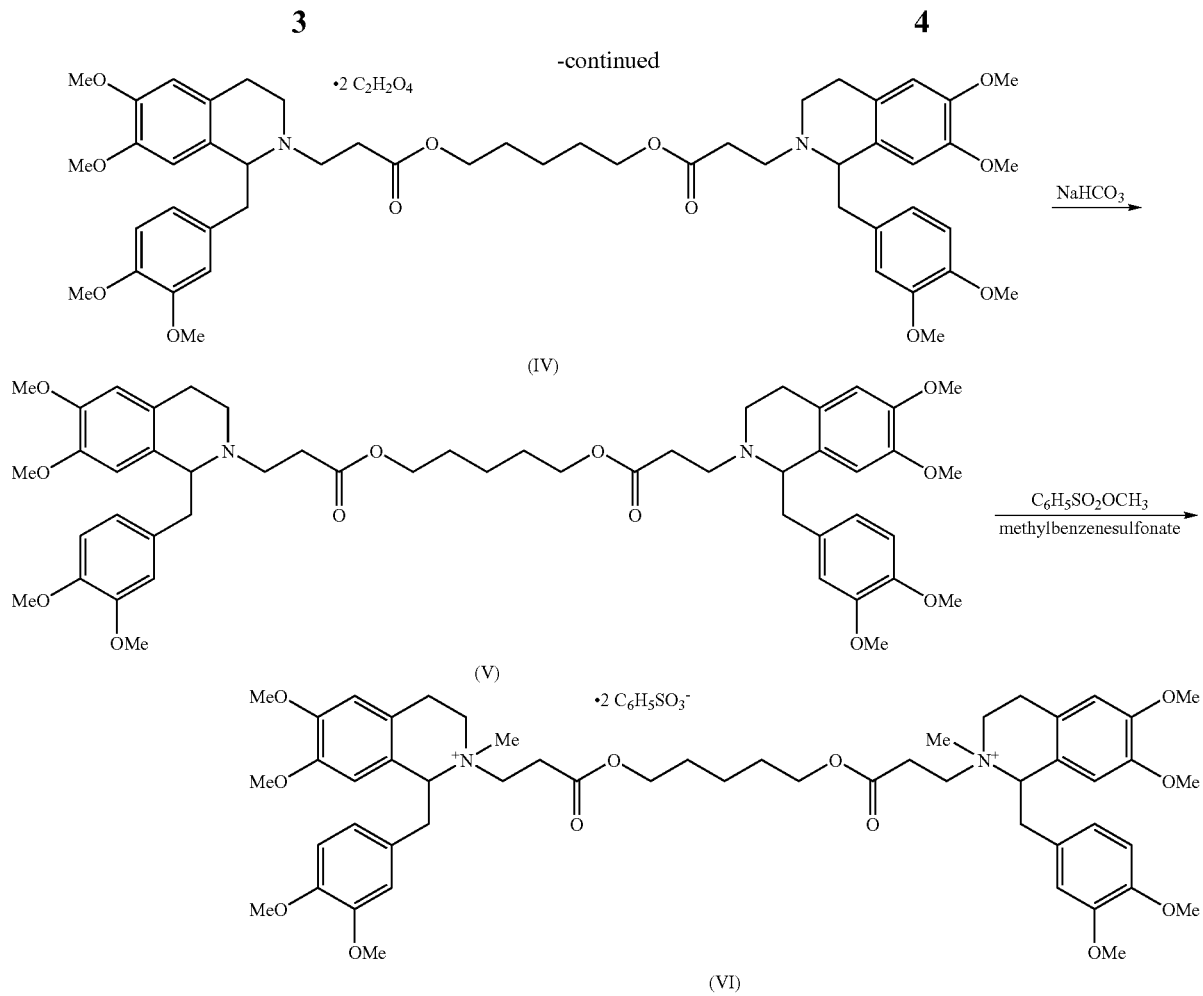

U.S. '507 discloses that the stereoisomerism of atracurium besylate (VI) may be partly controlled by controlling stereochemical configuration of compound (II) to provide the tertiary amine base (V) of a RR-, SS-, or RS-(meso) configuration. The quaternization process introduces 2 additional centers of asymmetry resulting in the formation of a mixture of stereoisomers. U.S. '507 does not describe separating stereoisomers from the mixture.

Cisatracurium besylate is disclosed in U.S. Pat. No. 5,453,510 (hereinafter U.S. '510). U.S. '510 describes the formation of (R)-tetrahydro-papaverine (compound HA) from compound (II) which is converted into a mixture of R and S diastereoisomer salts with the chiral amino acid, N-acetyl-L-leucine, resulting in the formation of a mixture of 83% of the R and 17% of the S diastereoisomer. Crystallization of the mixture from acetone affords 97% (R)-tetrahydropapaverine-N-acetyl-L-leucinate and 3% (S)-tetrahydropapaverine-N-acetyl-L-leucinate which is converted into (R)-tetrahydropapaverine base. The (R)-tetrahydropapaverine is subsequently reacted with 1,5-pentamethylene diacrylate followed by oxalic acid to afford the dioxalate salt of (1R,1'R)-2,2'-(3,11-dioxo-4,10-dioxatridecamethylene)-bis-(1,2,3,4-tetrahydro-6,7-dimethoxy-1-veratrylisoquinoline) (i.e., an isomer of compound IV). Conversion of the dioxalate salt into the free base, followed by treatment with methyl benzenesulfonate, affords an aqueous solution of (1R,1'R)-atracurium besylate. Lyophilization results in a pale yellow solid that includes a mixture of three isomers, namely, 1R-cis,1'R-cis; 1R-cis,1'R-trans; 1R-trans,1'R-trans (hereinafter referred to as the "atracurium besylate mixture") in a ratio of about 58:34:6 respectively. The atracurium besylate mixture is subjected to preparative HPLC column chromatography on silica using a mixture of dichloromethane, methanol and benzenesulfonic acid in the ratio of 4000:500:0.25 as the eluent. The fractions containing the required isomer are collected and washed with water. The dichloromethane solution is evaporated to dryness, the residue dissolved in water and the pH of the solution adjusted to 3.5-4.0 with an aqueous solution of benzenesulfonic acid. The aqueous solution is lyophilized to afford cisatracurium besylate possessing an isomeric purity of about 99%.

U.S. Pat. No. 5,556,978 (hereinafter U.S. '978) recites a process for the preparation of cisatracurium compounds, including cisatracurium besylate, using high performance liquid chromatography with a silica stationary phase and a non aqueous mobile phase in the presence of a strong acid. The resulting product may contain less than 2% w/w of other geometrical and optical isomers based on the total weight of the relevant mixture.

The above procedures suffer from several disadvantages. A major problem in the procedures is attributable to the HPLC purification step. The need for HPLC purification is undesirable in a large-scale operation because only relatively small amounts of product can be purified at a time, it is expensive, time-consuming and generates large quantities of waste, e.g., waste solvents. This means that considerations with regards to safely disposing of the accumulated wastes are necessary. A further disadvantage with the above procedures is that cisatracurium besylate may be unstable in the eluent mixture used in the HPLC separation and, thus, can lead to the formation of decomposition products.

There is, therefore, a need for an improved process for the production of cisatracurium, e.g., cisatracurium besylate, and intermediates therefor. It is desirable that the procedure avoids, where possible, the need for purifying the intermediates as well as the cisatracurium product by column chromatography. It is also desirable that the process can be scaled up to enable the large scale production of cisatracurium.

BRIEF SUMMARY OF THE INVENTION

In one embodiment, the present invention provides novel isoquinolinium compounds having the structural formulae (VIII), (IX) and (X) and methods for converting the compounds into cisatracurium salts, e.g., cisatracurium besylate (I).

The present invention also provides a method for preparing novel isoquinolinium compounds having the structural formulas (VIII), (IX) and (X) that are useful intermediates for preparing cisatracurium salts, e.g., cisatracurium besylate (I). In one embodiment, the present invention provides compounds (VIII) and (IX) as solids which can be purified readily using conventional purification techniques. In another embodiment, compounds (VIII) and (IX) are obtained as crystalline solids possessing characteristic X-ray powder diffraction patterns.

In one embodiment, the present invention provides a process for preparing compound (VII) from (R)-tetrahydropapaverine (IIA) or a salt thereof as outlined in Scheme 2. An exemplary process for preparing compound (VII) includes the steps of:

(a) reacting (R)-tetrahydropapaverine (IIA) or a salt thereof with an acrylic acid derivative (XI) to produce the corresponding compound (X);
(b) reacting compound (X) with a methylating agent to produce the corresponding compound (VIII);
(c) optionally purifying compound (VIII);
(d) converting compound (VIII) into compound (VII); and
(e) optionally purifying compound (VII).

Compound (X) can be optionally purified by conversion into a salt (IX), e.g., by dissolving compound (X) in an organic solvent and adding an inorganic or organic acid to afford compound (IX). The resulting acid addition salt (IX) can be purified by precipitation and isolation from the resulting suspension. Compound (IX) can be converted back to compound (X), e.g., by dissolving compound (IX) in water, adding a base and an organic solvent, and isolating compound (X) from the organic layer.

Compounds (VII) and (VIII) can be purified using standard techniques, e.g., precipitation, crystallization, filtration, extraction, slurrying or any suitable combination of such methods. Compound (VIII) is preferably purified by crystallization using standard techniques. Compound (VIII) also can be purified by slurrying in an organic solvent, optionally at an elevated temperature, and subsequently collecting compound (VIII) as a purified product.

The crystalline Compound (VII) of the present invention also can be purified by slurrying in an organic solvent, optionally at an elevated temperature, and subsequently collecting compound (VII) as a purified solid. In addition, compound (VII) can be purified by dissolving in an organic solvent, adding another organic solvent in which compound (VII) is sparingly soluble to precipitate compound (VII), and collecting compound (VII) as a purified solid. In accordance with the present invention, compound (VII) can be used to synthesize cisatracurium and salts thereof, e.g., cisatracurium besylate (I).

In accordance with the present invention, compounds (VII) and (VIII) can be produced in greater than about 99% purity.

DETAILED DESCRIPTION OF THE INVENTION

Figure 1:
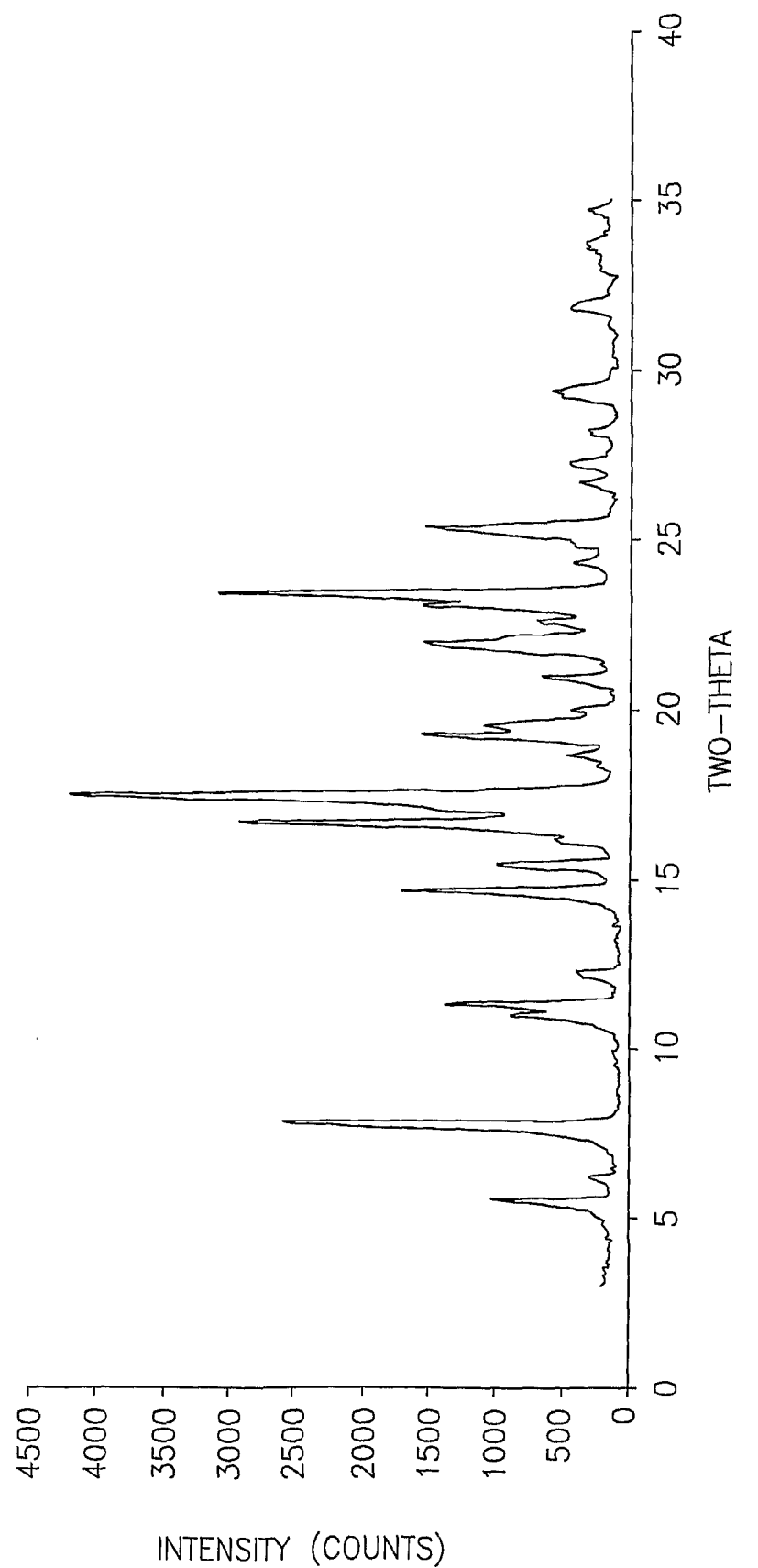
FIG. 1 illustrates the X-ray diffraction pattern for (1R)-1-[(3,4-dimethoxyphenyl)methyl]-1,2,3,4-tetrahydro-6,7-dimethoxy-2-tert-butoxycarbonylethyl-isoquinoline oxalate.

The present invention provides isoquinolinium compounds having the structural formulae (VII), (VIII), (IX) (an addition salt of (X)), and (X), and methods for converting the compounds into cisatracurium salt, e.g., cisatracurium besylate (I).

The compounds (VII), (VIII), (IX) and (X) can be obtained as solids. Compounds (VIII) and (IX) can be obtained as crystalline compounds possessing characteristic X-ray powder diffraction patterns and, thus, can be easily purified using conventional crystallization techniques. These compounds can be used to prepare cisatracurium besylate (I) in pure form without having to resort to complicated and expensive HPLC separation procedures as described in U.S. '510 and U.S. '978.

In one embodiment, the present invention provides a process for preparing the crystalline compound (VII) from (R)-tetrahydropapaverine, compound (IIA), or a salt thereof, as depicted in Scheme 2.

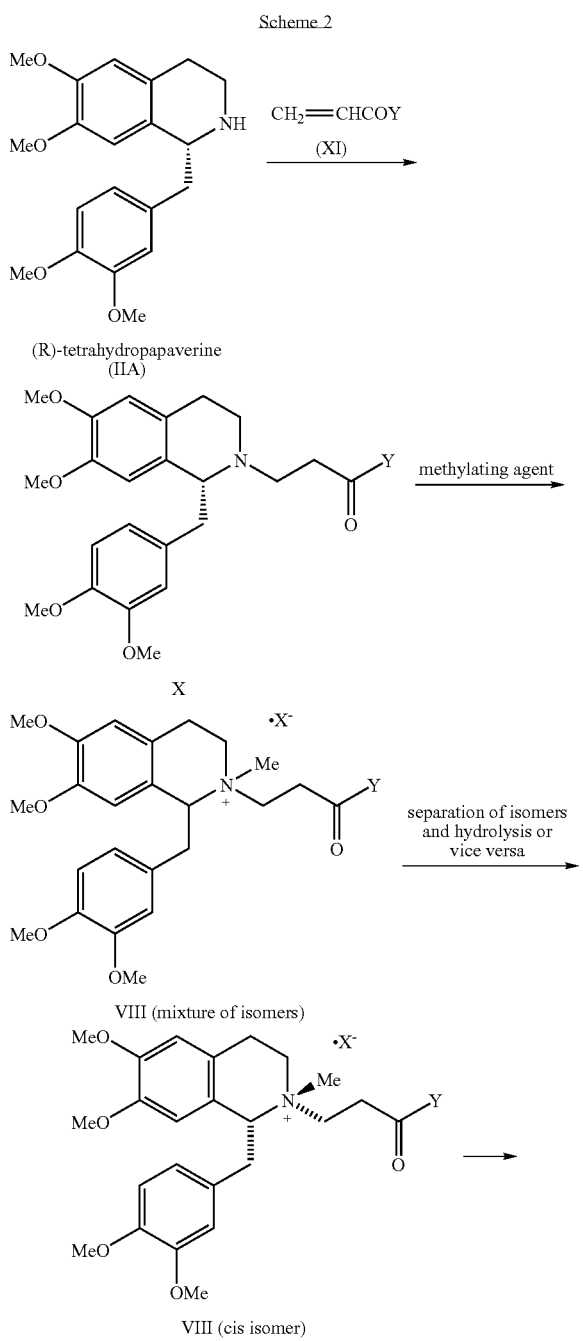

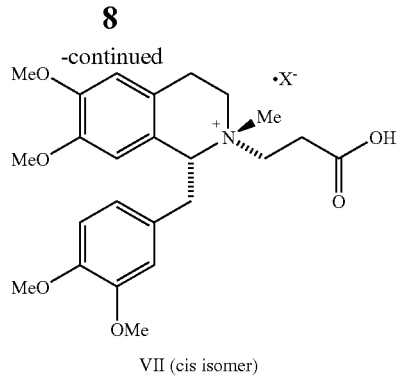

VII (cis isomer)

In accordance with the present invention, compound (VII), (1R-cis)-1-[(3,4-dimethoxyphenyl)methyl]-1,2,3,4-tetrahydro-6,7-dimethoxy-2-methyl-2-carboxyethyl-isoquinolinium salt, wherein $X^-$ is an anion, is preferably obtained by the following process:
  (a) reacting (R)-tetrahydropapaverine, compound IIA, or a salt thereof with an acrylic acid derivative (XI), in an organic solvent, to obtain compound (X);
  (b) reacting compound (X), or a salt thereof (IX), with a methylating agent to form compound (VIII);
  (c) optionally purifying compound (VIII);
  (d) converting compound (VIII) into compound (VII), and
  (e) optionally purifying compound (VII).

Step (a) preferably includes the steps of:
  (i) admixing compound (IIA) or a salt thereof with an acrylic acid derivative (XI) in an organic solvent; and
  (ii) heating the mixture of step (i) to obtain compound (X).

The organic solvent of step (i) can include, e.g., toluene, xylenes, ethyl acetate, dichloromethane, chloroform or a mixture thereof. A particularly preferred organic solvent is toluene.

For the acrylic acid derivative $CH_2$=CHCOY (XI), Y is $OR_1$ or $NR_2R_3$, wherein $R_1$ is un-substituted alkyl, aryl or heteroaryl, and $R_2$ and $R_3$ are the same or different and each is independently hydrogen, alkyl, aryl or heteroaryl.

For compound (X), Y is preferably $OR_1$ or $NR_2R_3$, wherein $R_1$, $R_2$ and $R_3$ are the same or different and each is preferably selected from hydrogen, alkyl, aryl and heteroaryl. Y of compound (X) is preferably $OR_1$ or $NR_2R_3$, $R_1$ is alkyl, aryl or heteroaryl, wherein $R_2$ and $R_3$ are the same or different and each is independently hydrogen, alkyl, aryl or heteroaryl.

The term "alkyl," as used herein, means linear, branched or cyclic hydrocarbon structures, containing from 1 to 20 carbon atoms, and combinations thereof. Lower alkyl refers to alkyl groups of from 1 to about 5 carbon atoms. Examples of lower alkyl groups include methyl, ethyl, propyl, isopropyl, butyl, sec- and t-butyl and the like. Preferred alkyl groups include about 6 or fewer carbon atoms. Cycloalkyl and bridged alkyl are a subset of alkyl and include cyclic hydrocarbon groups of from 3 to about 13 carbon atoms. Examples of cycloalkyl groups include cyclopropyl, cyclobutyl, cyclopentyl, norbornyl, adamantly and the like. The term "alkyl," as used herein, also refers to unsaturated alkyls such as, for example, alkanyl, alkenyl and alkynyl residues (e.g., vinyl, allyl, isoprenyl, and the like), and also refers to cycloalkyl-substituted alkyls (e.g., cyclohexylmethyl and the like).

The term "aryl" and "heteroaryl," as used herein, means a monocyclic or polycyclic aromatic group (e.g., phenyl or naphthyl) or a heteroaromatic ring containing 0-3 heteroatoms selected from O, N or S. Unless otherwise indicated, the aryl and the heteroaryl groups can be un-substituted or substituted with one or more, and in particular one to four groups independently selected from, for example, halo, $C_1$-$C_6$ alkyl, $OCF_3$, $NO_2$, CN and $OC_1$-$C_6$ alkyl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

In accordance with the present invention, compound (X) can be optionally purified, e.g., by reacting compound (X) with an inorganic or organic acid, optionally in an organic solvent, to afford compound (IX) as an acid addition salt of compound (X), and isolating compound (IX) from the resulting suspension, e.g., as a precipitate.

Exemplary organic solvents that can be used in the acid addition reaction to prepare compound (IX) include toluene, xylenes, benzene, ethyl acetate, dichloromethane, chloroform or a mixture thereof. A particularly preferred organic solvent for use in the acid addition reaction is toluene.

The inorganic or organic acid can include hydrogen chloride, hydrogen bromide, hydrogen iodide, methanesulfonic acid, benzenesulfonic acid, p-toluenesulfonic acid, naphthalene-1-sulfonic acid, naphthalene-2-sulfonic acid, oxalic acid or tartaric acid. A preferred organic acid is oxalic acid.

Exemplary compounds of the formula (IX) include:
(1R)-1-[(3,4-dimethoxyphenyl)methyl]-1,2,3,4-tetrahydro-6,7-dimethoxy-2-tert-butoxycarbonylethyl-isoquinolinium oxalate,
(1R)-1-[(3,4-dimethoxyphenyl)methyl]-1,2,3,4-tetrahydro-6,7-dimethoxy-2-aminocarbonylethyl-isoquinolinium oxalate,
(1R)-1-[(3,4-dimethoxyphenyl)methyl]-1,2,3,4-tetrahydro-6,7-dimethoxy-2-methoxycarbonylethyl-isoquinolinium oxalate,
(1R)-1-[(3,4-dimethoxyphenyl)methyl]-1,2,3,4-tetrahydro-6,7-dimethoxy-2-benzyloxycarbonylethyl-isoquinolinium oxalate, and
(1R)-1-[(3,4-dimethoxyphenyl)methyl]-1,2,3,4-tetrahydro-6,7-dimethoxy-2-tert-butylaminocarbonylethyl-isoquinolinium oxalate.

According to a preferred embodiment of the present invention, compound (IX) is isolated as a crystalline solid possessing a characteristic X-ray diffraction pattern.

Compound (IX) can be converted back to compound (X) by reaction with base, e.g., by combining compound (IX) with water, a base and an organic solvent, separating the layers and isolating compound (X) from the organic layer. Optionally, the organic layer can be dried, e.g., by adding a suitable drying agent. The base includes ammonium hydroxide, sodium hydroxide, potassium hydroxide, lithium hydroxide, sodium carbonate, potassium carbonate, or any suitable combination thereof. A preferred base is ammonium hydroxide.

In a preferred embodiment, the pH of the aqueous layer in the conversion of (IX) into (X) is from about 9 to about 12. The organic solvent for isolating (X) includes toluene, xylenes, ethyl acetate, dichloromethane, chloroform, or a mixture thereof. A particularly preferred organic solvent for isolating (X) is toluene. The organic layer can be dried with a suitable drying agent such as sodium sulfate, magnesium sulfate, calcium chloride or calcium sulfate. A particularly preferred drying agent is magnesium sulfate. The drying also can be performed by azeotropic distillation of the organic solvent.

Step (b) includes the steps of:
(i) reacting compound (X) with a methylating agent, optionally in an organic solvent, to produce compound (VIII); and
(ii) isolating compound (VIII).

The methylating agent used in step (b)(i) preferably includes dimethylcarbonate, dimethylsulfate, iodomethane, bromomethane, methyl triflate, methyl benzenesulfonate, trimethyloxonium tetrafluoroborate or methyl fluorosulfonate. Particularly preferred methylating agents are iodomethane and methyl benzenesulfonate.

The organic solvent that may be used in step (b)(i) can be selected from toluene, xylenes, ethyl acetate, dichloromethane, chloroform, acetonitrile, dimethyl sulfoxide (DMSO) and mixtures thereof. The reaction can be carried out without a solvent, that is, the methylating agent, e.g., iodomethane, serves as the reactant as well as the solvent. In some other embodiments the reaction can be carried out in an at least one organic solvent such as dichloromethane, acetonitrile or a mixture of dichloromethane and DMSO with methylating agents such as methyl benzenesulfonate (methyl besylate).

Step (b)(ii) preferably includes isolating compound (VIII) by e.g., filtration.

Compound (VIII) has the structural formula described in Scheme 2, wherein $X^-$ is an anion and Y is $OR_1$ or $NR_2R_3$, $R_1$, $R_2$ and $R_3$ are the same or different and each is independently selected from hydrogen, alkyl, aryl, and heteroaryl, with the proviso that Y is not OH. $R_1$ is alkyl, aryl or heteroaryl; $R_2$ and $R_3$ are independently hydrogen, alkyl, aryl or heteroaryl, and $X^-$ is an anion. Exemplary anions $X^-$ of compound (VIII) include chloride, bromide, iodide, methanesulfonate, benzenesulfonate, p-toluenesulfonate, naphthalene-1-sulfonate, naphthalene-2-sulfonate, tetrafluoroborate, oxalate and tartarate. A particularly preferred anion is benzenesulfonate.

In accordance with the present invention, compound (VIII) can be conveniently purified e.g., by slurrying or by selective crystallization of a mixture of isomers of compound (VIII) to separate the mixture of isomers.

In one embodiment, compound (VIII) can be purified by slurrying in at least one organic solvent, optionally at an elevated temperature, and collecting compound (VIII) as a purified product. The at least one organic solvent used for purifying compound (VIII) by slurrying method includes diethyl ether, diisopropyl ether, tert-butyl methyl ether, or a mixture thereof. A preferred organic solvent for slurrying compound (VIII) is diethyl ether.

Compound (VIII) also can be purified by crystallization or precipitation, e.g., by dissolving it in a first organic solvent and adding a second organic solvent in which compound (VIII) is sparingly soluble to precipitate compound (VIII). Exemplary first organic solvents include methanol, tetrahydrofuran (THF), acetone, dichloromethane, ethyl acetate and mixtures thereof. Exemplary second organic solvents in which compound (VIII) is sparingly soluble include diethyl ether, hexane, heptane, cyclohexane, and the like. In some embodiments compound (VIII) can be purified by crystallization or precipitation from one organic solvent, e.g., THF or acetone.

According to a preferred embodiment of the present invention, compound (VIII) is obtained as a crystalline solid possessing a characteristic X-ray diffraction pattern.

Exemplary compounds of formula (VIII) include the following:
(1R-cis)-1-[(3,4-dimethoxyphenyl)methyl]-1,2,3,4-tetrahydro-6,7-dimethoxy-2-methyl-2-tert-butoxycarbonylethyl-isoquinolinium iodide,
(1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate, (1R-cis)-1-[(3,4-dimethoxyphenyl)methyl]-1,2,3,4-tetrahydro-6,7-dimethoxy-2-methyl-2-aminocarbonylethyl-isoquinolinium iodide, (1R-cis)-1-[(3,4-dimethoxyphenyl)methyl]-1,2,3,4-tetrahydro-6,7-dimethoxy-2-methyl-2-methoxycarbonylethyl-isoquinolinium iodide, and (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate.

Step (d) includes converting compound (VIII) into compound (VII). In one embodiment, step (d) includes the steps of:

(i) hydrolyzing compound (VIII) e.g., by reacting it with an inorganic or an organic acid, or with a suitable silylating agent, or by carrying out hydrogenolysis, preferably in a solvent, to thereby produce compound (VII); and (ii) isolating compound (VII).

Exemplary solvents that can be used in the step (d)(i) hydrolysis include organic solvents and/or water. Exemplary organic solvents that can be used in step (d)(i) hydrolysis include acetone, methyl ethyl ketone, dichloromethane, chloroform, 1,2-dichloroethane, and mixtures thereof. A particularly preferred organic solvent for use in step (d)(i) hydrolysis is dichloromethane.

Exemplary inorganic or organic acids (including acidic ion exchange resins) that can be used in the step (d)(i) hydrolysis include hydrochloric acid, hydrobromic acid, hydroiodic acid, tetrafluoroboric acid, sulfuric acid, phosphoric acid, trifluoroacetic acid (TFA), methanesulfonic acid, benzenesulfonic acid, p-toluenesulfonic acid, Amberlyst®15 hydrogen form, Amberlite®IR120 hydrogen form or Amberjet®1200 hydrogen form. Preferred organic acids (including acidic ion exchange resins) are TFA, and Amberlyst®15 hydrogen form.

Compound (VIII) (wherein Y is not OH) optionally can be reacted with a halotrimethylsilane in an organic solvent. Exemplary halotrimethylsilanes that can be reacted with compound (VIII) include chlorotrimethylsilane, bromotrimethylsilane and iodotrimethylsilane. In another embodiment, the halotrimethylsilane comprises iodotrimethylsilane. In a preferred embodiment, the organic solvent used for reacting compound (VIII) with a halotrimethylsilane is a chlorinated hydrocarbon. A particularly preferred organic solvent for use in step (d)(i) is dichloromethane.

Compound (VIII) (wherein Y is $OR_1$ and $R_1$ is an unsubstituted or substituted benzyl) optionally can be reacted with hydrogen in the presence of a reduction catalyst and an organic solvent to produce the corresponding carboxylic acid. Exemplary reduction catalysts include palladium, palladium hydroxide, platinum and platinum oxide. Preferably, the reduction catalyst is palladium on activated carbon, e.g., from about 1% Pd to about 10% Pd on activated carbon, more preferably about 5% palladium on activated carbon. Exemplary organic solvents that can be used in the hydrogenolysis and which can optionally contain water include methanol, ethanol, isopropanol, n-propanol and mixtures thereof. A particularly preferred organic solvent for use in the hydrogenolysis is methanol.

In accordance with the present invention, compound (VII) can be conveniently purified e.g., by selective crystallization of compound (VII) from a mixture of isomers produced by hydrolyzing compound (VIII). Compound (VII) of step (ii) is preferably isolated by filtration.

According to a preferred embodiment of the present invention, compound (VII) is isolated as a crystalline solid. The crystalline Compound (VII) of the present invention has the structural formula depicted in Scheme 2, wherein $X^-$ is an anion of compound (VII), which includes chloride, bromide, iodide, methanesulfonate, benzenesulfonate, p-toluenesulfonate, naphthalene-1-sulfonate, naphthalene-2-sulfonate, tetrafluoroborate, oxalate or tartarate. Particularly preferred anion components $X^-$ of compound (VII) include benzenesulfonate, iodide and tetrafluoroborate.

The present invention provides a process for producing compound (VII) in greater than about 98% purity, and preferably greater than about 99% purity, as measured by HPLC.

Compound (VII) can be purified by any suitable method. In one embodiment of the present invention, compound (VII) is purified by a process that includes the steps of:

(i) admixing compound (VII) with an organic solvent;

(ii) optionally heating the mixture of step (i) to an elevated temperature; and (iii) collecting compound (VII) in a purified form.

Exemplary organic solvents that can be used for purifying compound (VII) according to step (i) include alcohols, ketones, esters, ethers, aromatic hydrocarbons, and chlorinated hydrocarbons, such as: methanol, ethanol, isopropanol, acetone, methyl ethyl ketone, ethyl acetate, isopropyl acetate, diethyl ether, tert-butyl methyl ether, tetrahydrofuran, toluene, xylenes, dichloromethane, chloroform, or a mixture thereof. A particularly preferred organic solvent for purifying compound (VII) according to step (i) is methanol. Compound (VII) can be isolated by filtration.

In another embodiment, compound (VII) is purified by dissolving it in a first organic solvent and adding a second organic solvent in which compound (VII) is sparingly soluble to precipitate compound (VII). Exemplary first organic solvents that can be used as solvents in the precipitation process include diethylether, isopropyl ether and mixtures thereof. A particularly preferred organic solvent is diethyl ether.

Exemplary second organic solvents in which compound (VII) is sparingly soluble include $C_5$ to $C_{12}$ saturated hydrocarbons such as hexane, heptane, cyclohexane, petroleum ether, and the like, and mixtures thereof.

The present invention further provides a process for producing cisatracurium salts, e.g., cisatracurium besylate which includes converting compound VII or a salt thereof into a cisatracurium salt, e.g., cisatracurium besylate. In one embodiment, the process for producing cisatracurium salt in accordance with the present invention includes coupling compound VII (e.g., about 2 equivalents) with 1,5-pentanediol ($HO(CH_2)_5OH$), to produce cisatracurium, and optionally isolating the cisatracurium salt, e.g., cisatracurium besylate. The coupling process can be carried out using any suitable method. In one embodiment, the coupling process includes activating the carboxylic acid of compound VII, and reacting the activated compound with 1,5-pentanediol. Compound VII can be activated using any suitable method, e.g., by converting compound VII into the corresponding acid halide (e.g., acid chloride), activated ester, or by any other suitable methods, including methods that can be used for esterifying carboxylic acids. In accordance with the present invention, compound (VII) can be used to synthesize cisatracurium besylate (I) without having to resort to difficult HPLC purification or other conventional procedures, e.g., as described in U.S. '510 and U.S. '978.

EXAMPLES

Reference is now made to the following examples, which, together with the above description, illustrate the invention in a non limiting fashion. Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Example 1

This example describes the preparation of (1R)-1-[(3,4-dimethoxyphenyl)-methyl]-1,2,3,4-tetrahydro-6,7-dimethoxy-2-tert-butoxycarbonylethyl-isoquinoline oxalate.

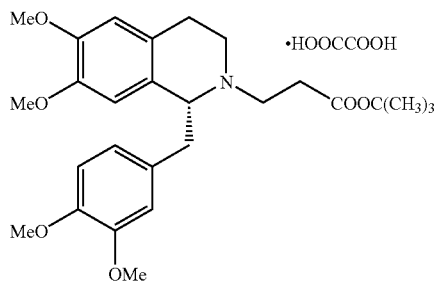

(R)-Tetrahydropaverine hydrochloride (20 g, 0.0527 moles) was dissolved in water (80 ml) and 25% aqueous ammonium hydroxide solution was added to produce a pH in the range of 9-10. Toluene (140 ml) was added and the mixture was stirred for 15 minutes at ambient temperature (about 25° C.). The upper organic layer was separated and washed with 10% sodium chloride solution. The organic layer was dried over magnesium sulfate and, subsequently, concentrated to about 50 ml. Tert-butyl acrylate (9.3 ml, 0.0636 moles) and glacial acetic acid (1.6 ml, 0.0267 moles) were added to the concentrated solution. The resulting mixture was heated to 80° C. and stirred at 80° C. for 5 hours. Subsequently, the mixture was cooled to ambient temperature and a solution of oxalic acid dihydrate (7.4 g, 0.0587 moles) in acetone (35 ml) was added to afford a suspension. Ethyl acetate (100 ml) was added to the suspension and the mixture was stirred at ambient temperature for 15 minutes. The suspension was filtered, washed with ethyl acetate and dried at 50° C. to afford (1R)-1-[(3,4-dimethoxyphenyl)methyl]-1,2,3,4-tetrahydro-6,7-dimethoxy-2-tert-butoxycarbonylethyl-isoquinoline oxalate, 26 g; (88% yield); m.p. 165°-168° C.; $[\alpha]_D$ −70.8° (c=1.00, DMSO); ESI$^+$ MS (m/z): 472.1 [MH$^+$].

The characteristic X-ray diffraction peaks are at the following peak positions (2θ): 7.8, 11.3, 14.7, 16.7, 17.5, 19.3, 19.6, 22.0, 23.1, 23.4, and 25.5. FIG. 1 depicts the X-ray powder diffraction pattern.

Figure 8:
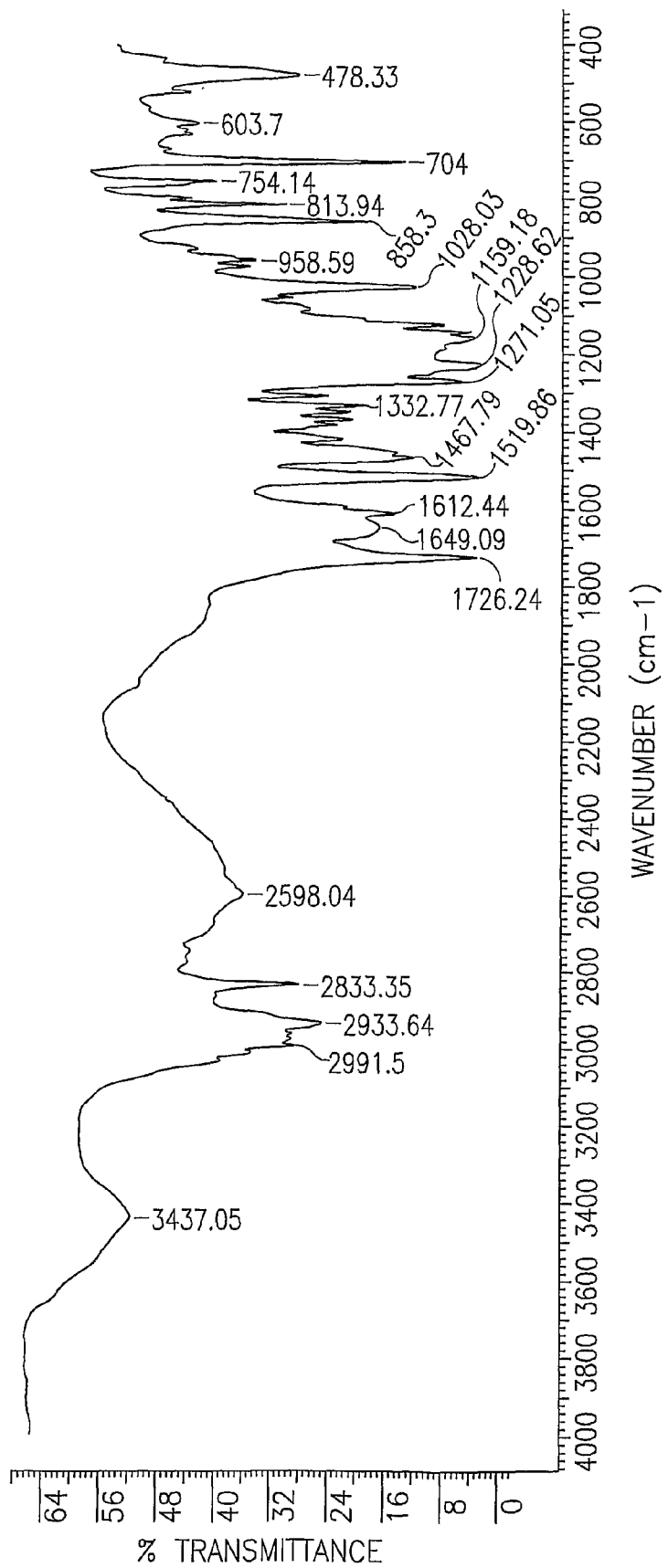
FIG. 8 illustrates the infrared spectrum for (1R)-1-[(3,4-dimethoxyphenyl)methyl]-1,2,3,4-tetrahydro-6,7-dimethoxy-2-tert-butoxycarbonylethyl-isoquinoline oxalate.

The characteristic infrared absorption bands are at 3437.05, 2991.50, 2933.64, 2833.35, 2598.04, 1726.24, 1649.09, 1612.44, 1519.86, 1467.79, 1332.77, 1271.05, 1228.62, 1159.18, 1028.03, 958.59, 858.30, 813.94, 754.14, 704.00, 603.70, 478.33 cm$^{-1}$. The infrared spectrum is depicted in FIG. 8.

Example 2

This example describes the preparation of (1R)-1-[(3,4-dimethoxyphenyl)methyl]-1,2,3,4-tetrahydro-6,7-dimethoxy-2-aminocarbonylethyl-isoquinoline oxalate.

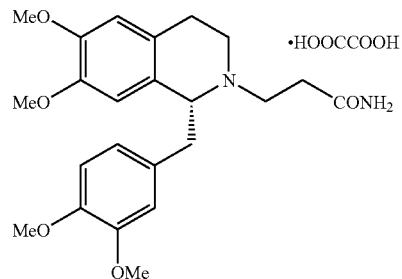

(R)-Tetrahydropaverine hydrochloride (30 g, 0.079 moles) was dissolved in water (120 ml) and 25% aqueous ammonium hydroxide solution was added to produce a pH in the range of 9-10. Toluene (200 ml) was added and the mixture was stirred for 15 minutes at ambient temperature. The upper organic layer was separated and washed with 10% sodium chloride solution. The organic layer was dried over magnesium sulfate and, subsequently, concentrated to about 70 ml. Acrylamide (6.72 g, 0.0946 moles) and glacial acetic acid (2.4 ml, 0.04 moles) were added to the concentrated solution. The resulting mixture was heated to 80° C. and stirred at 80° C. for 5 hours. Subsequently, the mixture was cooled to ambient temperature and a solution of oxalic acid dihydrate (11 g, 0.0873 moles) in acetone (50 ml) was added to afford a suspension. Ethyl acetate (100 ml) was added to the suspension and the mixture was stirred at ambient temperature for 15 minutes. The suspension was filtered, washed with ethyl acetate and dried at 50° C. to afford 40.1 g of crude (1R)-1-[(3,4-dimethoxyphenyl)methyl]-1,2,3,4-tetrahydro-6,7-dimethoxy-2-aminocarbonylethyl-isoquinoline oxalate.

The crude sample was crystallized from methanol:ethyl acetate (1:1) mixture (200 ml) to afford pure (1R)-1-[(3,4-dimethoxyphenyl)methyl]-1,2,3,4-tetrahydro-6,7-dimethoxy-2-aminocarbonylethyl-isoquinoline oxalate, 37 g; (93% yield); m.p. 115°-118° C.; $[\alpha]_D$ −48.5° (c=1.00, H$_2$O); ESI$^+$ MS (m/z): 415.1 [MH$^+$].

The characteristic X-ray diffraction peaks are at the following peak positions (2θ): 7.8, 10.2, 15.4, 17.4, 18.1, 20.2, 21.5, 23.5, 24.3, 25.5, 27.1.

Figure 2:
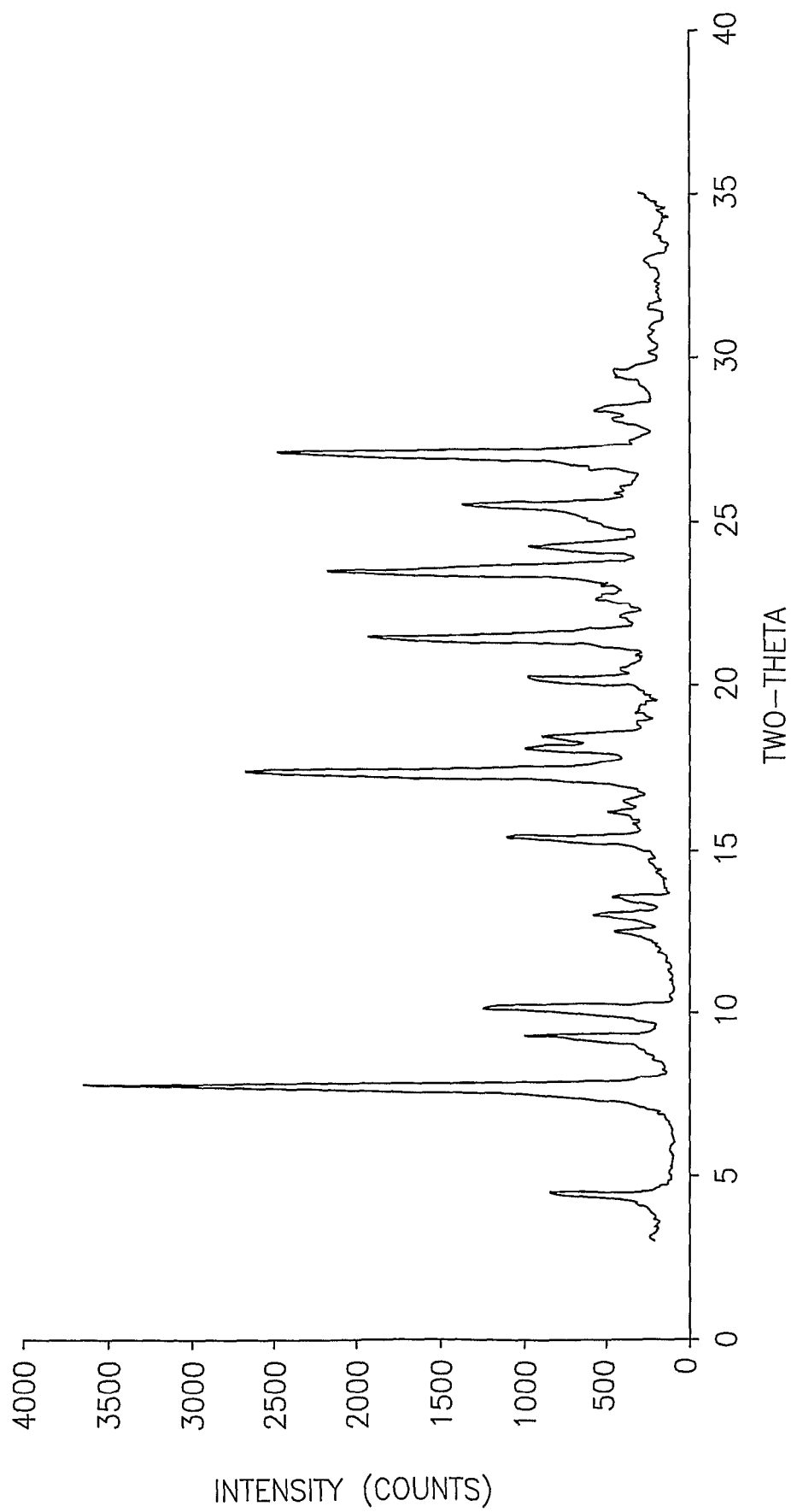
FIG. 2 illustrates the X-ray diffraction pattern for (1R)-1-[(3,4-dimethoxyphenyl)methyl]-1,2,3,4-tetrahydro-6,7-dimethoxy-2-aminocarbonylethyl-isoquinoline oxalate.

FIG. 2 depicts the X-ray powder diffraction pattern.

Figure 9:
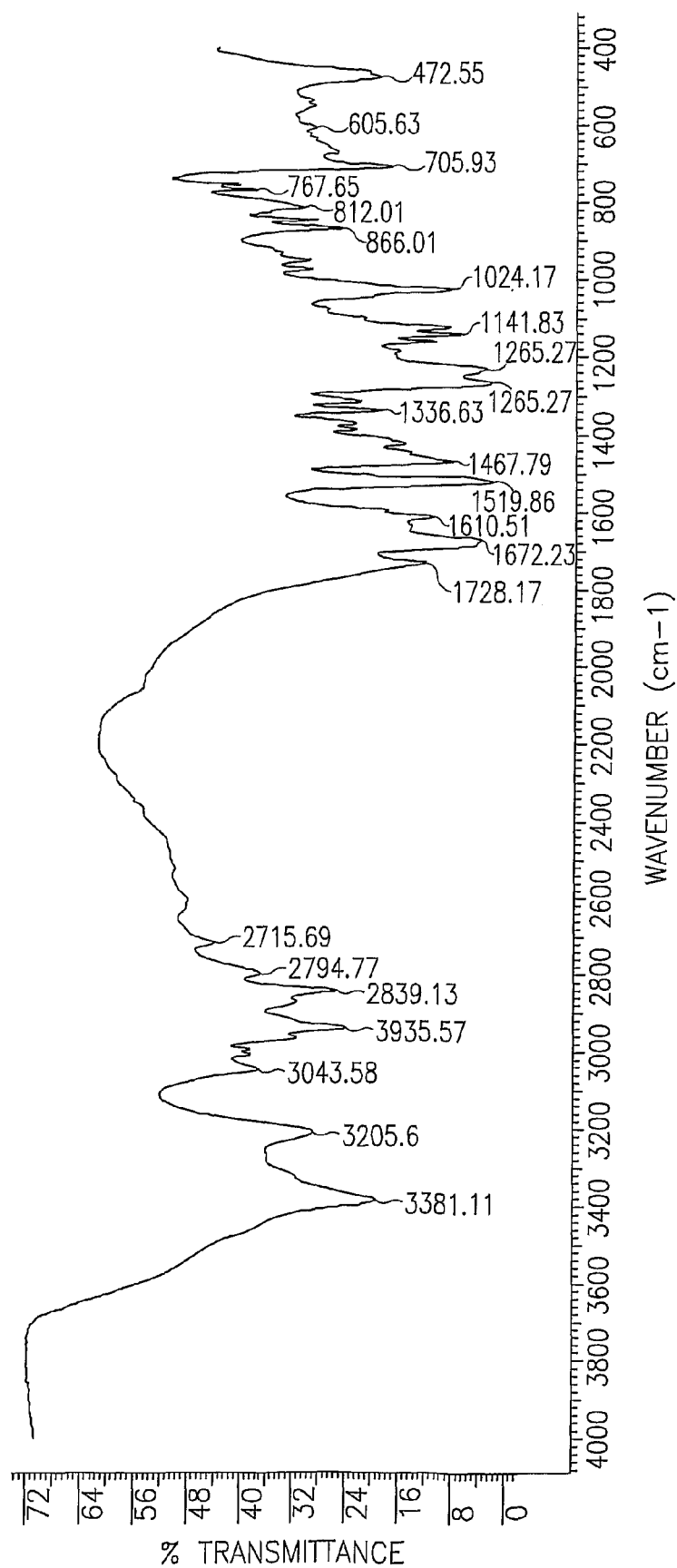
FIG. 9 illustrates the infrared spectrum for (1R)-1-[(3,4-dimethoxyphenyl)methyl]-1,2,3,4-tetrahydro-6,7-dimethoxy-2-aminocarbonylethyl-isoquinoline oxalate.

The characteristic infrared absorption bands are at 3381.11, 3205.60, 3043.58, 2935.57, 2839.13, 2794.77, 2715.69, 1728.17, 1672.23, 1610.51, 1519.86, 1467.79, 1336.63, 1265.27, 1230.55, 1141.83, 1024.17, 866.01, 812.01, 767.65, 705.93, 605.63, 472.55 cm$^{-1}$. The infrared spectrum is depicted in FIG. 9.

Example 3

This example describes the preparation of (1R)-1-[(3,4-dimethoxyphenyl)methyl]-1,2,3,4-tetrahydro-6,7-dimethoxy-2-methoxycarbonylethyl-isoquinoline oxalate.

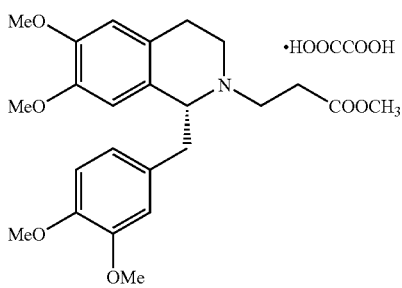

(R)-Tetrahydropaverine hydrochloride (25 g, 0.0658 moles) was dissolved in water (100 ml) and 25% aqueous ammonium hydroxide solution was added to produce a pH in the range of 9-10. Dichloromethane (100 ml) was added and the mixture was stirred for 15 minutes at about 25° C. The upper organic layer was separated. The procedure was repeated by extracting with dichloromethane (3×100 ml) another 3 times. The combined organic layer was washed with 10% sodium chloride solution. The organic layer was dried over magnesium sulfate and, subsequently, evaporated to dryness under reduced pressure to afford a residual oil. To the residual oil was added benzene (50 ml), methyl acrylate (10 g, 0.1163 moles) and glacial acetic acid (1.3 ml, 0.0217 moles). The mixture was heated at 80° C. for 4 hours. Subsequently, the mixture was cooled to ambient temperature and a solution of oxalic acid dihydrate (9.2 g, 0.0730 moles) in acetone (45 ml) was added. To the resulting suspension was added ethyl acetate (100 ml). The precipitate was filtered, washed with ethyl acetate and dried at 50° C. to afford (1R)-1-[(3,4-dimethoxyphenyl)methyl]-1,2,3,4-tetrahydro-6,7-dimethoxy-2-methoxycarbonylethyl-isoquinoline oxalate 29.2 g; (85% yield); m.p. 141°-142° C., $[\alpha]_D$ −60.3° (c=1.01, water).

Example 4

This example describes the preparation of (1R)-1-[(3,4-dimethoxyphenyl)-methyl]-1,2,3,4-tetrahydro-6,7-dimethoxy-2-benzyloxycarbonylethyl-isoquinoline oxalate.

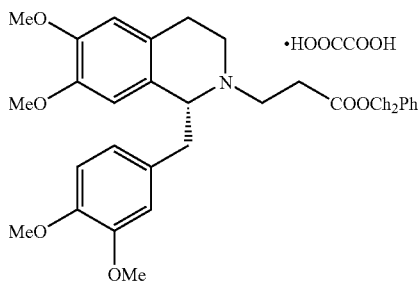

(R)-Tetrahydropaverine hydrochloride (30 g, 0.0790 moles) was dissolved in water (120 ml) and 25% aqueous ammonium hydroxide solution was added to produce a pH in the range of 9-10. Toluene (200 ml) was added and the mixture was stirred for 15 minutes at ambient temperature. The upper organic layer was separated. The procedure was repeated by extracting with toluene another 2 times (2×200 ml). The combined organic layer was washed with 10% sodium chloride solution. The organic layer was dried over magnesium sulfate and, subsequently, evaporated to dryness under reduced pressure to afford a residual oil. To the oil was added toluene (100 ml), benzyl acrylate (14.3 ml, 0.0888 moles) and glacial acetic acid (2.5 ml, 0.0417 moles). The mixture was heated at 80° C. for 4 hours. Subsequently, the mixture was cooled to ambient temperature and a solution of oxalic acid dihydrate (11.0 g, 0.0873 moles) in acetone (50 ml) was added. The mixture was stirred for 1 hour and the precipitate was filtered, washed with ethyl acetate (50 ml). The solid was collected. Methanol (200 ml) was added and the mixture was heated to reflux to afford a solution, which was hot-filtered. The filtrate was cooled to ambient temperature and kept at this temperature for 2 hours. The precipitate was collected by filtration, washed with ethyl acetate (3×50 ml) and dried at 60° C. to afford (1R)-1-[(3,4-dimethoxyphenyl)methyl]-1,2,3,4-tetrahydro-6,7-dimethoxy-2-benzyloxy-carbonylethyl-isoquinoline oxalate 35.5 g; (76% yield); m.p. 144°-147° C.; $[\alpha]_D$ −59.1° (c=1.00, DMSO); ER$^+$ MS (m/z): 506.3 [MH$^+$].

The characteristic X-ray diffraction peaks are at the following peak positions (2θ): 5.2, 7.8, 14.0, 17.3, 17.6, 18.8, 20.3, 21.1, 21.7, 23.5, 25.7.

Figure 3:
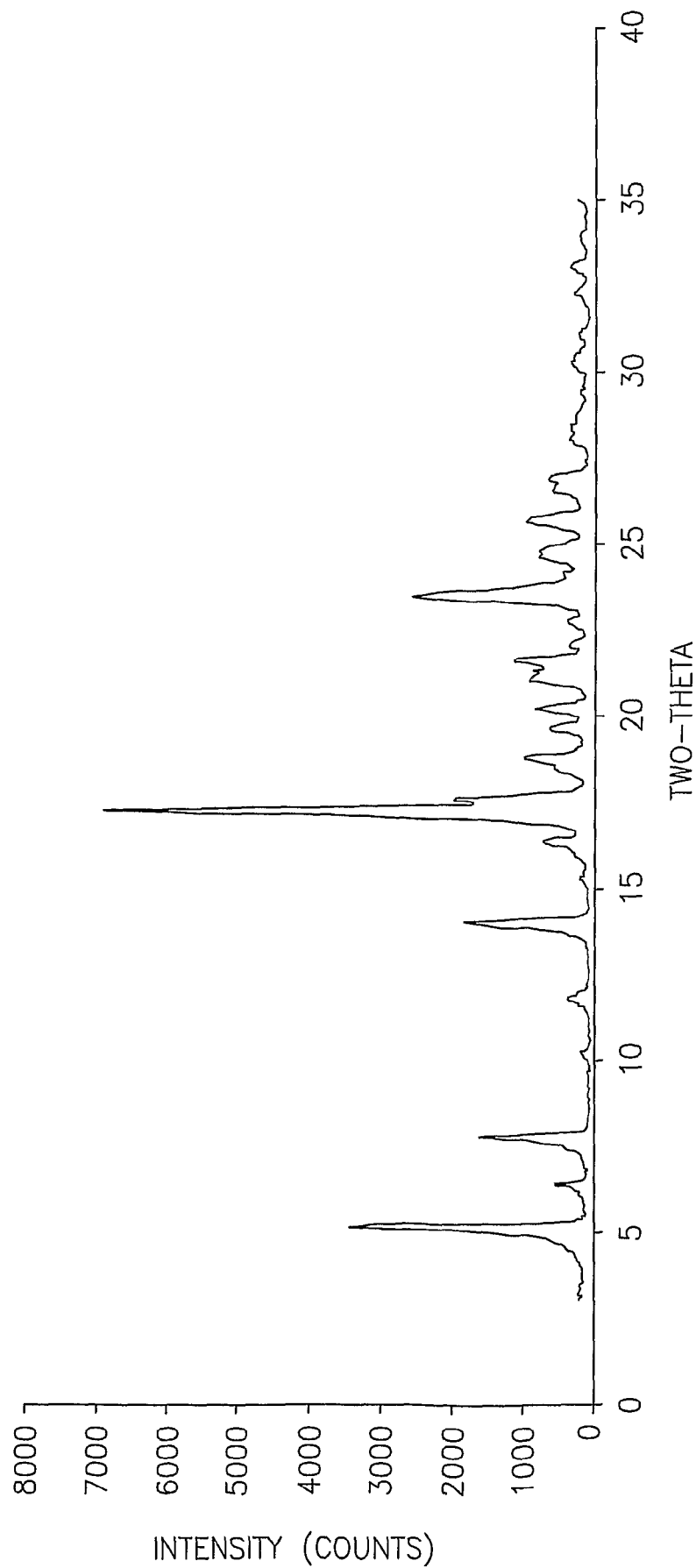
FIG. 3 illustrates the X-ray diffraction pattern for (1R)-1-[(3,4-dimethoxyphenyl)methyl]-1,2,3,4-tetrahydro-6,7-dimethoxy-2-benzyloxycarbonylethyl-isoquinoline oxalate.

FIG. 3 depicts the X-ray powder diffraction pattern.

The characteristic infrared absorption bands are at 3435.12, 3016.58, 2945.21, 2835.28, 2596.11, 1747.46, 1643.30, 1610.51, 1517.93, 1456.21, 1419.57, 1369.42, 1342.42, 1267.19, 1228.62, 1143.75, 1124.47, 1082.03, 1022.24, 966.31, 860.23, 821.65, 756.07, 734.86, 705.93, 626.85, 474.47, 426.26 cm$^{-1}$.

Figure 10:
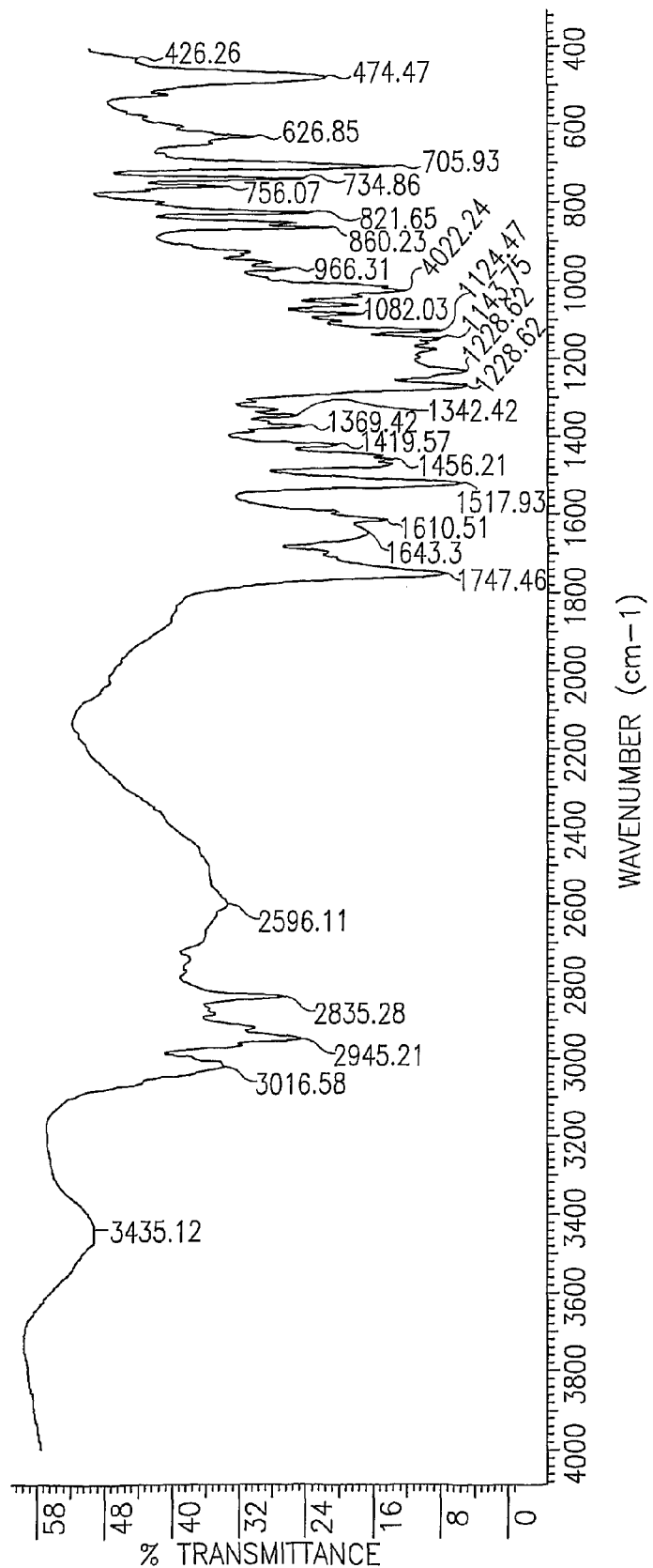
FIG. 10 illustrates the infrared spectrum for (1R)-1-[(3,4-dimethoxyphenyl)methyl]-1,2,3,4-tetrahydro-6,7-dimethoxy-2-benzyloxycarbonylethyl-isoquinoline oxalate.

FIG. 10 depicts the infrared spectrum.

Example 4A

This example describes the preparation of (1R)-1-[(3,4-dimethoxyphenyl)-methyl]-1,2,3,4-tetrahydro-6,7-dimethoxy-2-benzyloxycarbonylethyl-isoquinoline oxalate.

(R)-Tetrahydropaverine hydrochloride (45 g, 0.118 moles) was dissolved in water (240 ml) and 25% aqueous ammonium hydroxide solution (20 ml) was added to produce a pH in the range of 9-10. Toluene (300 ml) was added and the mixture was stirred for 15 minutes at ambient temperature. The upper organic layer was separated. The procedure was repeated by extracting with toluene another 2 times (2×300 ml). The organic layer was dried over magnesium sulfate (25 g) and, subsequently, evaporated to dryness under reduced pressure to afford a residual oil (42.5 g). To the oil was added toluene (150 ml), benzyl acrylate (24.3 g, 0.0.149 moles) and glacial acetic acid (3.7 ml, 0.059 moles). The mixture was heated at 80° C. for 3.5 hours. The reaction mixture was diluted with toluene (100 ml).

Subsequently, the mixture was cooled to ambient temperature and a solution of anhydrous oxalic acid (15.6 g, 0.0144 moles) in acetone (100 ml) was added. The mixture was stirred at ambient temperature for 2 hours. The precipitate was filtered and washed with diethyl ether (60 ml). The solid was collected to afford the crude product. The crude product was admixed with methanol (400 ml) and the mixture was heated to reflux to afford a solution. The hot solution was clarified by filtration. The filtrate was cooled to ambient temperature and kept at this temperature for 2 hours. The precipitate was collected by filtration, washed with diethyl ether and dried at about 60° C. to afford (1R)-1-[(3,4-dimethoxyphenyl)methyl]-1,2,3,4-tetrahydro-6,7-dimethoxy-2-benzyloxycarbonylethyl-isoquinoline oxalate, 52.3 g; (75% yield), HPLC purity: 97%.

Example 5

This example describes the preparation of (1R)-1-[(3,4-dimethoxyphenyl)-methyl]-1,2,3,4-tetrahydro-6,7-dimethoxy-2-tert-butylaminocarbonylethyl-isoquinoline oxalate.

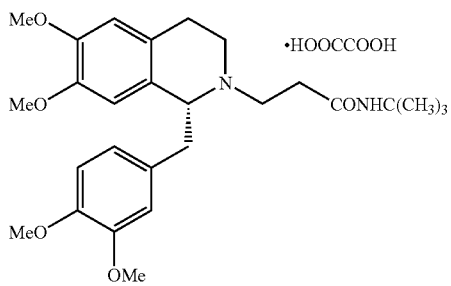

(R)-Tetrahydropaverine hydrochloride (30 g, 0.0790 moles) was dissolved in water (120 ml) and 25% aqueous ammonium hydroxide solution was added to produce a pH in the range of 9-10. Toluene (140 ml) was added and the mixture was stirred for 15 minutes at ambient temperature. The upper organic layer was separated and washed with 10% sodium chloride solution. The organic layer was dried over magnesium sulfate and concentrated to a volume of 75 ml. N-tert-butyl acrylamide (12 g, 0.094 moles) and glacial acetic acid (2.5 ml, 0.0417 moles) were added and the mixture was heated at 80° C. for 20 hours. Subsequently, the mixture was cooled to ambient temperature and a solution of oxalic acid dihydrate (11.0 g, 0.0873 moles) in acetone (50 ml) was added. The mixture was stirred for 1 hour to form a suspension. Ethyl acetate (200 ml) was added and the thus formed precipitate was collected by filtration. Methanol (160 ml) was added and the solid was dissolved under reflux to form a solution. The mixture was cooled gradually to 5° C. overnight. The thus formed precipitate was collected by filtration and the filtrate was concentrated to 80 ml under reduced pressure. Ethyl acetate (200 ml) was added and the mixture was stirred for two hours at ambient temperature. The thus formed solid was washed 3 times with ethyl acetate (3×50 ml) and dried at 60° C. to afford (1R)-1-[(3,4-dimethoxyphenyl)-methyl]-1,2,3,4-tetrahydro-6,7-dimethoxy-2-tert-butyl-aminocarbonylethyl-isoquinoline oxalate 27 g; (60% yield); m.p. 172°-175° C.; $[\alpha]_D$ −21.5° (c 1.00, $H_2O$); $ESI^+$ MS (m/z): 471.2 [$MH^+$].

The characteristic X-ray diffraction peaks are at the following peak positions (2θ): 5.4, 6.9, 12.6, 15.8, 17.4, 17.8, 19.3, 22.0, 22.5, 26.2, 26.8.

Figure 4:
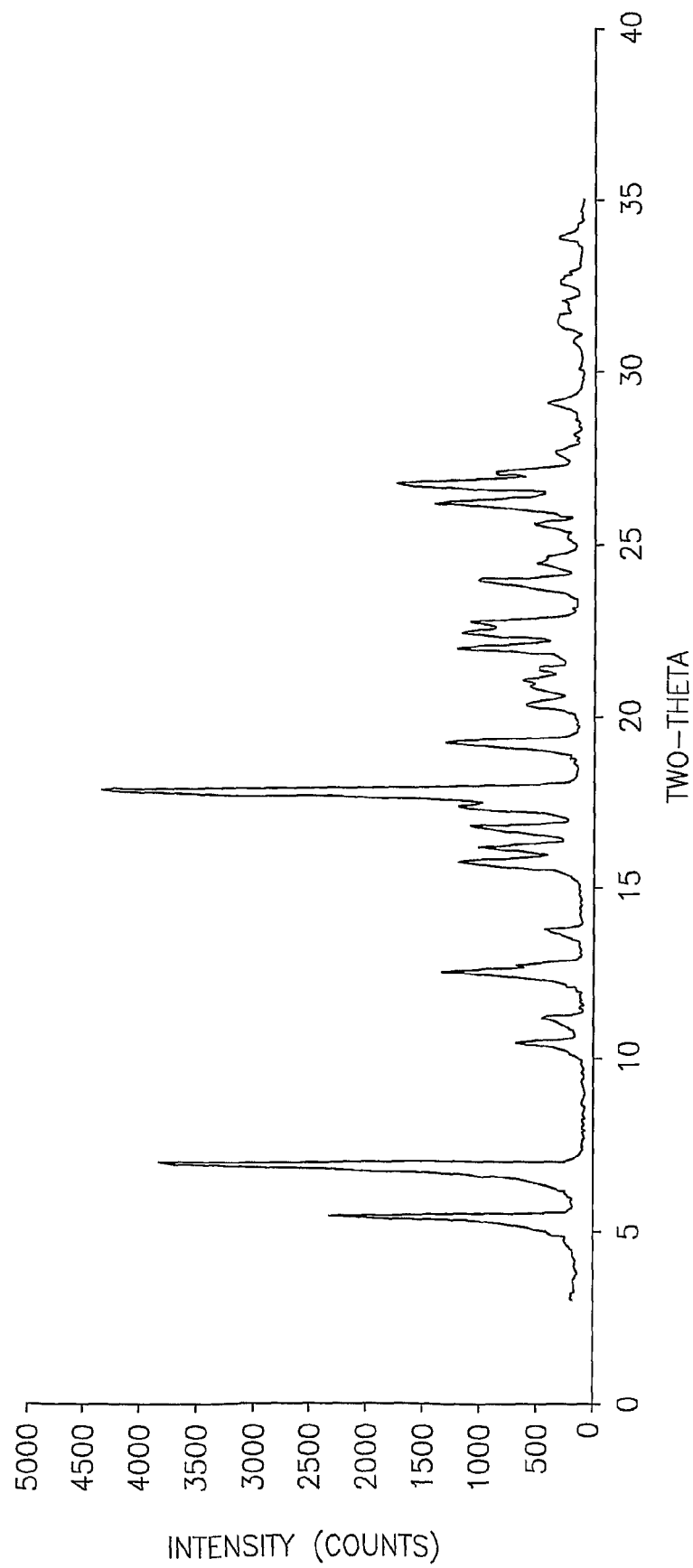
FIG. 4 illustrates the X-ray diffraction pattern for (1R)-1-[(3,4-dimethoxyphenyl)methyl]-1,2,3,4-tetrahydro-6,7-dimethoxy-2-tert-butylaminocarbonylethyl-isoquinoline oxalate.

FIG. 4 depicts the X-ray powder diffraction pattern.

The characteristic infrared absorption bands are at 3440.91, 3290.46, 2962.57, 2931.71, 2831.42, 2594.18, 1753.24, 1654.88, 1610.51, 1517.93, 1465.86, 1388.71, 1365.56, 1263.34, 1230.55, 1141.83, 1122.54, 1028.03, 948.95, 864.08, 810.08, 704.00, 624.92, 484.12 $cm^{-1}$.

Figure 11:
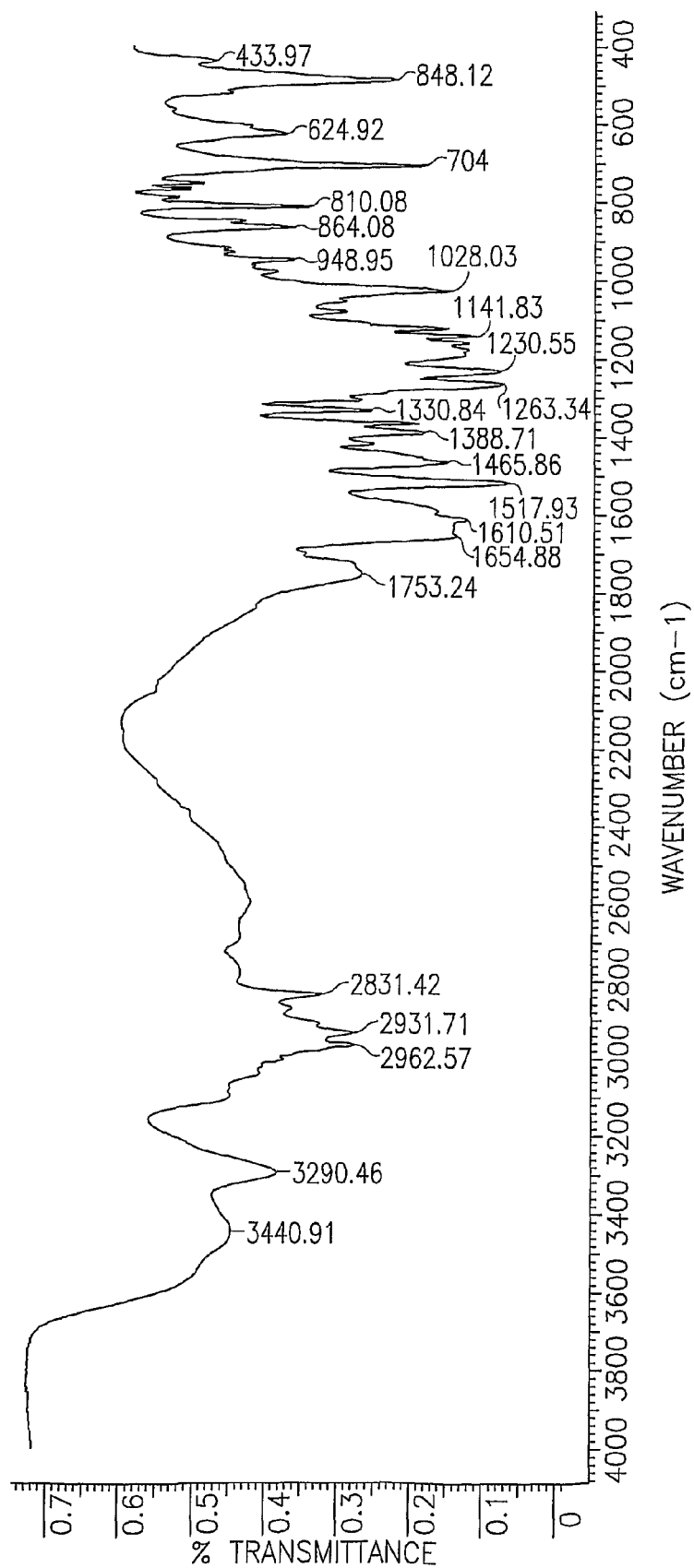
FIG. 11 illustrates the infrared spectrum for (1R)-1-[(3,4-dimethoxyphenyl)methyl]-1,2,3,4-tetrahydro-6,7-dimethoxy-2-tert-butylaminocarbonylethyl-isoquinoline oxalate.

FIG. 11 depicts the infrared spectrum.

The following examples illustrate the preparation of quaternary ammonium salts of esters and amides from the tertiary amine bases prepared according to examples 1-5.

Example 6

This example describes the preparation of a mixture of the cis and trans isomers of (1R)-1-[(3,4-dimethoxyphenyl)methyl]-1,2,3,4-tetrahydro-6,7-dimethoxy-2-methyl-2-tert-butoxycarbonylethyl-isoquinolinium iodide.

(1R)-1-[(3,4-dimethoxyphenyl)methyl]-1,2,3,4-tetrahydro-6,7-dimethoxy-2-tert-butoxycarbonylethylisoquinoline oxalate (7.0 g, 0.0125 moles), prepared as described in example 1, was dissolved in water (50 ml) and 25% aqueous ammonium hydroxide solution was added to produce a pH in the range of 9-10. Toluene (100 ml) was added and the mixture was stirred for 15 minutes at ambient temperature. The upper organic layer was separated and washed with 10% sodium chloride solution. The organic layer was dried over magnesium sulfate and the solvent was evaporated under reduced pressure to afford a solid residue. Iodomethane (30 ml, 0.482 moles) was added to the residue and the mixture was stirred to obtain a solution and kept at ambient temperature overnight. The resulting precipitate was collected by filtration, washed with diethyl ether and dried at room temperature to afford a mixture of 81.5% of the cis and 18.5% of the trans isomers of (1R)-1-[(3,4-dimethoxyphenyl)methyl]-1,2,3,4-tetrahydro-6,7-dimethoxy-2-methyl-2-tert-butoxycarbonylethyl-isoquinolinium iodide (5.5 g; 72% yield).

Example 6A

This example describes the preparation of (1R-cis)-1-[(3,4-dimethoxyphenyl)-methyl]-1,2,3,4-tetrahydro-6,7-dimethoxy-2-methyl-2-tert-butoxycarbonylethyl-isoquinolinium iodide by crystallization of isomeric mixture.

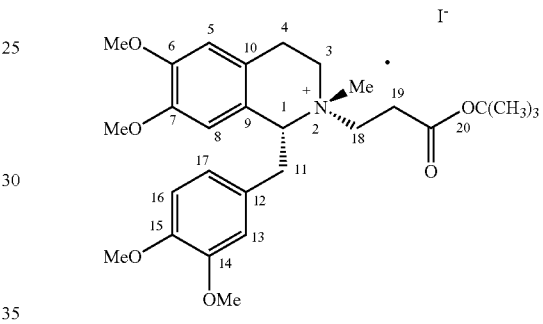

A mixture of the cis and the trans isomers of (1R)-1-[(3,4-dimethoxy-phenyl)methyl]-1,2,3,4-tetrahydro-6,7-dimethoxy-2-methyl-2-tert-butoxycarbonylethylisoquinolinium iodide (1.0 g), prepared as detailed in example 6, was admixed with methanol (1.5 ml) and heated to obtain a solution. Ethyl acetate (10 ml) was added to the solution. The mixture was cooled to ambient temperature and stirred for 1 hour at 25° C. Subsequently, the mixture was cooled to 5° C. and kept at 5° C. overnight. The thus formed crystals were collected by filtration, washed with ethyl acetate and dried to afford (1R-cis)-1-[(3,4-dimethoxyphenyl)methyl]-1,2,3,4-tetrahydro-6,7-dimethoxy-2-methyl-2-tert-butoxycarbonyl-ethyl-isoquinolinium iodide, 0.7 g, (70% yield or 86% yield from the cis isomer), HPLC purity 97.6% with 2.4% of the trans isomer, m.p. 180°-183° C. (dec.), $[\alpha]_D$ −61.5° (c=1.05, $CH_2Cl_2$)

$^1H$ NMR ($CDCl_3$): δ=1.48 (s, 9H, t-butyl), 3.00 (m, 1H, $H_{11}$), 3.09-3.20 (m, 3H, $H_{11}$, $H_{19}$, and $H_4$), 3.31 (s, 3H, NMe), 3.24-3.33 (m, 2H, $H_{19}$ and $H_4$), 3.49 (s, 3H, $OCH_3$), 3.62-3.75 (m, 1H, $H_3$), 3.79 (s, 3H, $OCH_3$), 3.82 (s, 3H, $OCH_3$), 3.84 (s, 3H, $OCH_3$), 4.08 (m, 2H, $H_{18}$ and $H_3$), 4.31 (m, 1H, $H_{18}$), 5.28 (m, 1H, $H_1$), 6.11 (s, 1H, $H_8$), 6.53 (m, 1H, $H_{17}$), 6.62 (d, 1H, $H_{13}$), 6.67 (s, 1H, $H_5$), 6.73 (d, 1H, $H_{16}$). $^{13}C$ NMR ($CDCl_3$): δ=23.33 ($C_4$), 27.89 (C—$CH_3$), 29.22 ($C_{19}$), 37.64 ($C_{11}$), 47.05 ($NCH_3$), 53.96 ($C_3$), 55.62 ($OCH_3$), 55.71 ($OCH_3$), 55.85 ($OCH_3$), 56.33 ($OCH_3$), 58.9 ($C_{18}$), 70.64 ($C_1$), 82.62 ($CMe_3$), 110.42 ($C_5$), 111.00 ($C_{16}$), 111.79 ($C_8$), 113.24 ($C_{13}$), 120.07 ($C_{10}$), 121.02 ($C_9$), 122.39 ($C_{17}$), 126.36 ($C_{12}$), 147.02 ($C_6$), 148.17 ($C_{14}$), 148.85 ($C_{15}$), 149.16 ($C_7$), 168.30 ($C_{20}$), $ESI^+$ MS (m/z): 486.2 [$M^+$].

Example 7

This example describes the preparation of a mixture of the cis and trans isomers of (1R)-1-[(3,4-dimethoxyphenyl)methyl]-1,2,3,4-tetrahydro-6,7-dimethoxy-2-methyl-2-tert-butoxycarbonylethyl-isoquinolinium iodide.

(1R)-1-[(3,4-dimethoxyphenyl)methyl]-1,2,3,4-tetrahydro-6,7-dimethoxy-2-tert-butoxycarbonylethyl-isoquinoline oxalate (1.0 g, 0.00178 moles) was dissolved in water (10 ml) and saturated aqueous sodium bicarbonate solution was added to produce a pH in the range of 9-10. Dichloromethane (20 ml) was added and the mixture was stirred for 15 minutes at ambient temperature. The upper organic layer was separated and the aqueous layer was extracted three times with dichloromethane (3×20 ml). The combined organic layer was dried over magnesium sulfate. The organic layer was evaporated under reduced pressure to afford a residual oil. Iodomethane (8 ml, 0.128 moles) was added to the oily residue and the mixture was stirred to obtain a solution and kept at room temperature overnight. The reaction mixture was added to diethyl ether (50 ml) to afford a suspension, which was stirred at ambient temperature for 30 minutes. The thus formed solid was collected by filtration, washed with diethyl ether (2×5 ml) and dried to afford a mixture of 70% of the cis and 30% of the trans isomers of (1R)-1-[(3,4-dimethoxyphenyl)methyl]-1,2,3,4-tetrahydro-6,7-dimethoxy-2-methyl-2-tert-butoxycarbonylethyl-isoquinolinium iodide (0.95 g; 89% yield).

Example 7A

This example describes the preparation of (1R-cis)-1-[(3,4-dimethoxyphenyl)-methyl]-1,2,3,4-tetrahydro-6,7-dimethoxy-2-methyl-2-tert-butoxycarbonylethyl-isoquinolinium iodide by flash chromatography of the isomeric mixture.

A mixture of the cis and the trans isomers of (1R)-1-[(3,4-dimethoxyphenyl)-methyl]-1,2,3,4-tetrahydro-6,7-dimethoxy-2-methyl-2-tert-butoxycarbonylethylisoquinolinium iodide (0.4 g), prepared as detailed in example 7, was applied to a silica gel column (silica gel 60, 230-400 mesh, 14.0 g) and flash chromatographed eluting with dichloromethane:2-propanol:methanol in a ratio of 20:1:0.25. The solution of the product in the eluent mixture was evaporated under reduced pressure to afford (1R-cis)-1-[(3,4-dimethoxyphenyl)methyl]-1,2,3,4-tetrahydro-6,7-dimethoxy-2-methyl-2-tert-butoxycarbonyl-ethyl-isoquinolinium iodide 0.24 g, (60% yield or 86% yield from the cis isomer), HPLC purity 100%.

The physical data of the product was identical to the physical data of the product obtained in example 6A.

Example 8

This example describes the preparation of a mixture of the cis and trans isomers of (1R)-1-[(3,4-dimethoxyphenyl)methyl]-1,2,3,4-tetrahydro-6,7-dimethoxy-2-methyl-2-aminocarbonylethyl-isoquinolinium iodide.

(1R)-1-[(3,4-dimethoxyphenyl)methyl]-1,2,3,4-tetrahydro-6,7-dimethoxy-2-aminocarbonylethylisoquinoline oxalate (7.0 g, 0.0139 moles) was dissolved in water (30 ml) and 20% aqueous sodium hydroxide solution was added to produce a pH in the range of 9-10. Dichloromethane (100 ml) was added and the mixture was stirred for 15 minutes at ambient temperature. The upper organic layer was separated and washed with 10% sodium chloride solution. The organic layer was dried over magnesium sulfate and evaporated under reduced pressure to afford an oily residue. Iodomethane (20 ml, 0.321 moles) was added to the oily residue. The mixture was stirred to obtain a solution and kept at ambient temperature overnight. The resulting precipitate was collected by filtration, washed with diethyl ether and dried to afford a mixture of 72% of the cis and 28% of the trans isomers of (1R)-1-[(3,4-dimethoxyphenyl)methyl]-1,2,3,4-tetrahydro-6,7-dimethoxy-2-methyl-2-aminocarbonylethyl-isoquinolinium iodide (7.7 g; 99% yield).

Example 8A

This example describes the preparation of (1R-cis)-1-[(3,4-dimethoxyphenyl)-methyl]-1,2,3,4-tetrahydro-6,7-dimethoxy-2-methyl-2-aminocarbonylethyl-isoquinolinium iodide by crystallization of isomeric mixture.

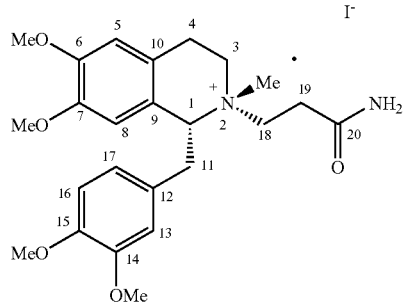

A mixture of the cis and the trans isomers of (1R)-1-[(3,4-dimethoxyphenyl)-methyl]-1,2,3,4-tetrahydro-6,7-dimethoxy-2-methyl-2-aminocarbonylethyl-isoquinolinium iodide (1.5 g), prepared as detailed in example 8, was admixed with methanol (6 ml) and heated to obtain a solution. The solution was cooled to ambient temperature and stirred at that temperature for 1 hour. Subsequently, the mixture was cooled to 5° C. and kept at that temperature overnight. The thus formed crystals were collected by filtration, washed with ethyl acetate and dried to afford (1R-cis)-1-[(3,4-dimethoxyphenyl)-methyl]-1,2,3,4-tetrahydro-6,7-dimethoxy-2-methyl-2-aminocarbonylethyl-isoquinolinium iodide, 0.85 g, (57% yield or 79% yield from the cis isomer), HPLC purity 97.2% with 2.8% of the trans isomer; m.p. 201°-203° C. (dec.), $[\alpha]_D$ −65.6° (c=1.02, DMSO).

$^1$H NMR (CDCl$_3$): δ=2.90-4.35 (m, 10H; H$_3$, H$_4$, H$_{11}$, H$_{18}$ and H$_{19}$), 3.21 (s, 3H, NMe), 3.39 (s, 3H, OCH$_3$), 3.74 (s, 3H, OCH$_3$), 3.76 (s, 3H, OCH$_3$), 3.82 (s, 3H, OCH$_3$), 5.00 (m, 1H, H$_1$), 5.87 (s, 1H, H$_8$), 6.53-6.67 (m, 4H; H$_5$, H$_{13}$, H$_{16}$ and H$_{17}$), 7.06 (s, 1H, NH$_2$) and 7.83 (s, 1H, NH$_2$). $^{13}$C NMR (CDCl$_3$): δ=23.46 (C$_4$), 29.67 (C$_{19}$), 37.66 (C$_{11}$), 47.21 (N CH$_3$), 54.10 (C$_3$), 55.67 (OCH$_3$), 55.92 (OCH$_3$), 55.99 (O CH$_3$), 56.69 (OCH$_3$), 59.76 (C$_{18}$), 70.82 (C$_1$), 110.60 (C$_5$), 111.21 (C$_{16}$), 112.13 (C$_8$), 113.81 (C$_{13}$), 120.25 (C$_{10}$), 121.04 (C$_9$), 123.6 (C$_{17}$), 126.70 (C$_{12}$), 146.94 (C$_6$), 148.29 (C$_{14}$), 148.93 (C$_{15}$), 149.28 (C$_7$), and 171.68 (C$_{20}$), ESI$^+$ MS (m/z): 429.2 [M$^+$].

The characteristic X-ray diffraction peaks are at the following peak positions (2θ): 4.8, 17.8, 18.3, 18.7, 21.1, 22.8, 24.5, 25.8, 28.3, 29.0.

Figure 5:
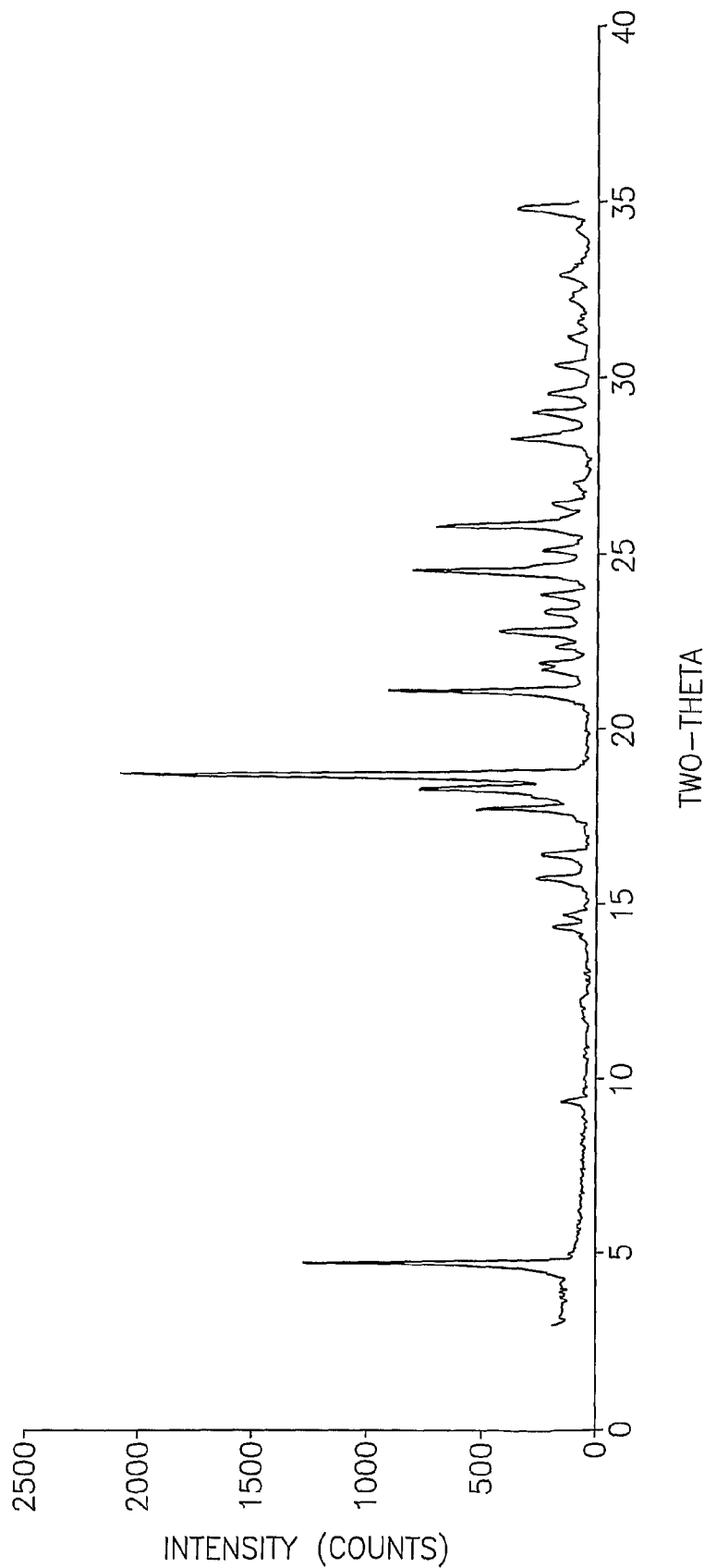
FIG. 5 illustrates the X-ray diffraction pattern for (1R-cis)-1-[(3,4-dimethoxyphenyl)-methyl]-1,2,3,4-tetrahydro-6,7-dimethoxy-2-methyl-2-aminocarbonylethyl-isoquinolinium iodide.

FIG. 5 depicts the X-ray powder diffraction pattern.

The characteristic infrared absorption bands are at 3342.54, 3230.67, 3157.38, 2962.57, 2925.93, 2835.28, 1679.95, 1608.58, 1516.00, 1448.50, 1382.92, 1255.62, 1230.55, 1157.26, 1118.68, 1020.31, 989.45, 954.74, 860.23, 817.79, 763.79, 632.63, 563.20, 497.62, 428.18 cm$^{-1}$.

Figure 12:
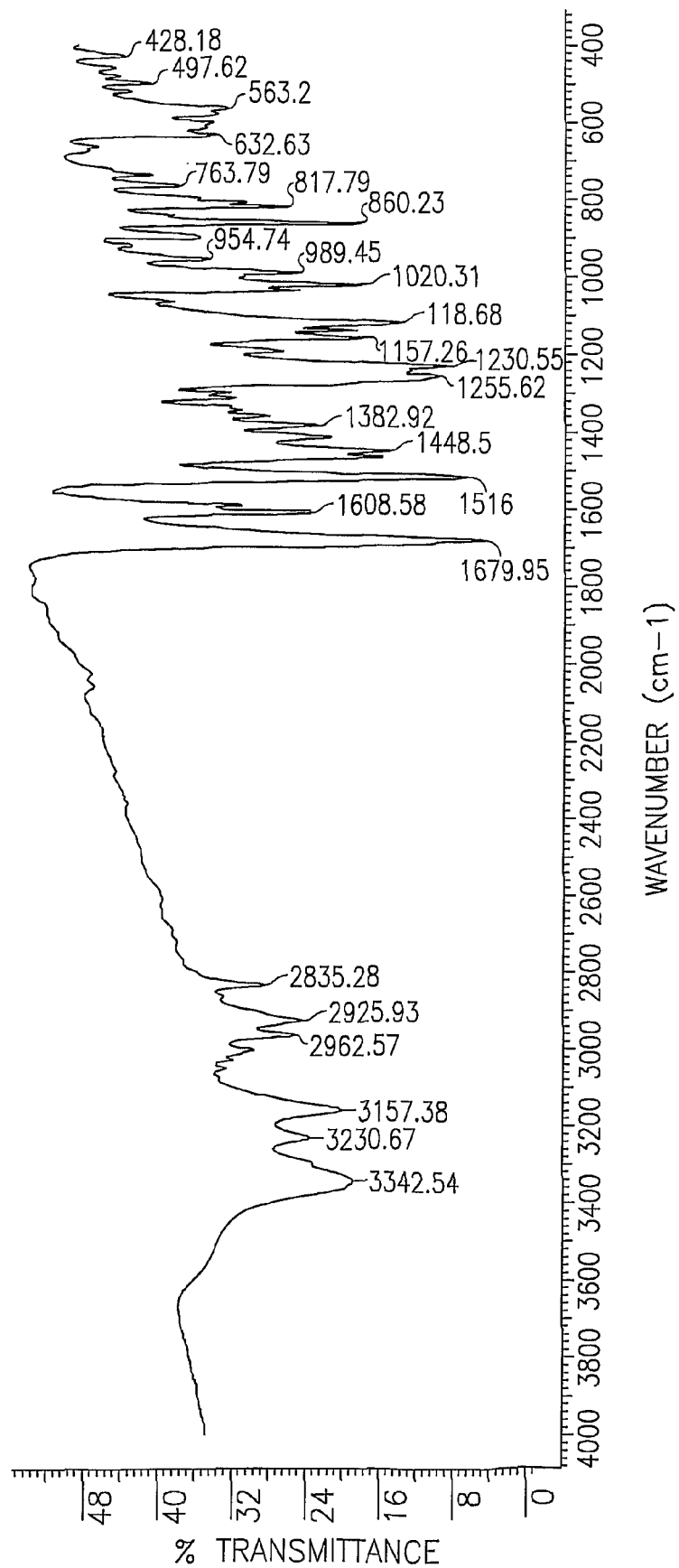
FIG. 12 illustrates the infrared spectrum for (1R-cis)-1-[(3,4-dimethoxyphenyl)methyl]-1,2,3,4-tetrahydro-6,7-dimethoxy-2-methyl-2-aminocarbonylethyl-isoquinolinium iodide.

FIG. 12 depicts the Infrared spectrum.

Example 9

This example describes the preparation of a mixture of the cis and trans isomers of (1R)-1-[(3,4-dimethoxyphenyl)methyl]-1,2,3,4-tetrahydro-6,7-dimethoxy-2-methyl-2-methoxycarbonylethyl-isoquinolinium iodide.

(1R)-1-[(3,4-dimethoxyphenyl)methyl]-1,2,3,4-tetrahydro-6,7-dimethoxy-2-methoxycarbonylethylisoquinoline oxalate (7.0 g, 0.0135 moles) was dissolved in water (50 ml) and aqueous sodium bicarbonate solution was added to produce a pH in the range of 9-10. Dichloromethane (100 ml) was added and the mixture was stirred for 15 minutes at that temperature. The upper organic layer was separated and the aqueous layer was extracted three times with dichloromethane (3×100 ml). The combined organic layer was dried over magnesium sulfate and washed with 10% sodium chloride solution. The organic layer was dried over magnesium sulfate and evaporated under reduced pressure to afford a residual oil. Iodomethane (30 ml, 0.482 moles) was added to the oily residue and the mixture was stirred to obtain a solution and kept at ambient temperature overnight. The reaction mixture was added to diethyl ether (100 ml) to afford a suspension. The suspension was stirred at ambient temperature for 30 minutes to afford a solid, which was collected by filtration, washed with diethyl ether (2×15 ml) and dried to afford a mixture of 70% of the cis and 30% of the trans isomers of (1R)-1-[(3,4-dimethoxyphenyl)methyl]-1,2,3,4-tetrahydro-6,7-dimethoxy-2-methyl-2-methoxycarbonylethyl-isoquinolinium iodide (5.9 g; 77% yield).

Example 9A

This example describes the preparation of (1R-cis)-1-[(3,4-dimethoxyphenyl)-methyl]-1,2,3,4-tetrahydro-6,7-dimethoxy-2-methyl-2-methoxycarbonylethyl-isoquinolinium besylate by ion exchange.

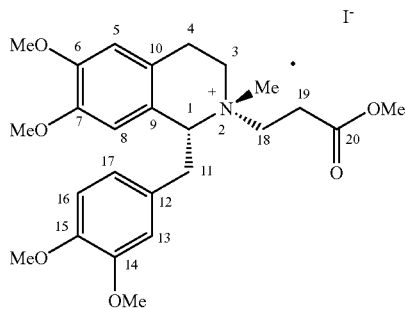

A mixture of cis and trans isomers of (1R)-1-[(3,4-dimethoxyphenyl)-methyl]-1,2,3,4-tetrahydro-6,7-dimethoxy-2-methyl-2-methoxycarbonylethyl-isoquinolinium iodide (1.0 g), prepared as detailed in example 9, was admixed with 0.2M aqueous benzenesulfonic acid solution (50 ml) to obtain a solution. The solution was applied to two ion exchange cartridges (HYPER SAX 10000 MG/75 ML/10 PKG; Cat. No. 60108-715). The cartridges were washed with 0.2M aqueous benzenesulfonic acid solution (400 ml). The combined aqueous solutions were extracted four times with dichloromethane (4×100 ml). The combined dichloromethane extracts was dried over magnesium sulfate and subsequently evaporated under reduced pressure to afford a solid consisting of a cis and trans mixture of (1R)-1-[(3,4-dimethoxyphenyl)methyl]-1,2,3,4-tetrahydro-6,7-dimethoxy-2-methyl-2-methoxycarbonylethyl-isoquinolinium besylate (0.85 g).

The product (0.85 g) was admixed with methanol (2 ml) and the mixture was heated to obtain a solution. Ethyl acetate (8 ml) was added to the solution and the mixture was cooled to ambient temperature and stirred for 1 hour. Subsequently, the mixture was cooled to 5° C. and kept at that temperature for 48 hours. The thus formed crystals were collected by filtration, washed with ethyl acetate and dried to afford (1R-cis)-1-[(3,4-dimethoxyphenyl)methyl]-1,2,3,4-tetrahydro-6,7-dimethoxy-2-methyl-2-methoxycarbonylethyl-isoquinolinium besylate, 0.31 g, (31% yield or 44% yield from the cis isomer), HPLC purity 100%; m.p. 187°-190° C.

$^1$H NMR (CDCl$_3$): δ=2.93 (dd, 1H; J=13.2, 9.3 Hz, H$_{11}$), 3.08 (m, 1H, H$_4$), 3.22-3.40 (m, 3H, H$_{19}$ and H$_4$), 3.30 (s, 3H, NCH$_3$), 3.45 (s, 3H, OCH$_3$), 3.61-3.67 (m, 1H, H$_{11}$), 3.71 (s, 3H, COOCH$_3$), 3.74 (s, 3H, OCH$_3$), 3.83 (s, 3H, OCH$_3$), 3.84 (s, 3H, OCH$_3$), 3.86-3.91 (m, 1H, H$_3$), 4.16 (m, 1H, H$_{18}$ and H$_3$), 4.31 (m, 1H, H$_{18}$), 5.01 (m, 1H, H$_1$), 5.97 (s, 1H, H$_8$), 6.44 (dd, 1H, J=7.8, 1.8 Hz, H$_{17}$), 6.56 (bs, 1H, H$_{13}$), 6.64 (s, 1H, H$_5$), 6.69 (d, 1H, J=7.8 Hz, H$_{16}$), 7.31-7.35 (m, 3H, besylate), 7.89 (dd, 2H, J=5.4, 2.1 Hz, besylate). ESI$^+$ MS (m/z): 444.2 [M$^+$].

Example 9B

This example describes the preparation of (1R-cis)-1-[(3,4-dimethoxy-phenyl)methyl]-1,2,3,4-tetrahydro-6,7-dimethoxy-2-methyl-2-methoxycarbonylethyl-isoquinolinium iodide by crystallization of isomeric mixture.

A mixture of the cis and the trans isomers of (1R)-1-[(3,4-dimethoxy-phenyl)methyl]-1,2,3,4-tetrahydro-6,7-dimethoxy-2-methyl-2-methoxycarbonylethyl-isoquinolinium iodide (1.0 g), prepared as described in example 9, was admixed with methanol (4 ml) and heated to obtain a solution. Ethyl acetate (6 ml) was added and the solution was cooled to about 25° C. and stirred for 1 hour. Subsequently, the mixture was cooled to 5° C. and kept at that temperature for 72 hours. The thus formed crystals were collected by filtration, washed with ethyl acetate and dried to afford (1R-cis)-1-[(3,4-dimethoxyphenyl)methyl]-1,2,3,4-tetrahydro-6,7-dimethoxy-2-methyl-2-methoxycarbonylethyl-isoquinolinium iodide, 0.315 g, (32% yield or 45% yield from the cis isomer), HPLC purity 99.6% with 0.4% of the trans isomer; m.p. 186°-188° C., [α]$_D$ −77.9° (c=1.02, CH$_2$Cl$_2$).

$^1$H NMR (CDCl$_3$): δ=2.99 (dd, 1H; J=13.8, 9.6 Hz, H$_{11}$), 3.12 (dd, 1H, J=18.6, 6.6 Hz, H$_4$), 3.22-3.40 (m, 3H, H$_{19}$ and H$_4$), 3.35 (s, 3H, NCH$_3$), 3.49 (s, 3H, OCH$_3$), 3.64 (dd, 1H, J=13.8, 4.2 Hz, H$_{11}$), 3.74 (s, 3H, COOCH$_3$), 3.73-3.77 (m, 1H, H$_3$), 3.80 (s, 3H, OCH$_3$), 3.82 (s, 3H, OCH$_3$), 3.85 (s, 3H, OCH$_3$), 4.16 (m, 2H, H$_{18}$ and H$_3$), 4.38 (m, 1H, H$_{18}$), 5.34 (dd, 1H, J=9.6, 4.2 Hz, H$_1$), 6.10 (s, 1H, H$_8$), 6.52 (dd, 1H, J=8.4, 1.8 Hz, H$_{17}$), 6.64 (d, 1H, J=1.8 Hz, H$_{13}$), 6.66 (s, 1H, H$_5$), 6.71 (d, 1H, J=8.4 Hz, H$_{16}$). $^{13}$C NMR (CDCl$_3$): δ=23.51 (C$_4$), 28.57 (C$_{19}$), 37.90 (C$_{11}$), 47.20 (NCH$_3$), 52.83 (COOCH$_3$), 54.14 (C$_3$), 55.82 (OCH$_3$), 55.94 (OCH$_3$), 56.05 (OCH$_3$), 56.62 (OCH$_3$), 58.93 (C$_{18}$), 70.85 (C$_1$), 110.60 (C$_5$), 111.22 (C$_{16}$), 112.02 (C$_8$), 113.44 (C$_{13}$), 120.22 (C$_{10}$), 121.29 (C$_9$), 122.65 (C$_{17}$), 126.54 (C$_{12}$), 147.26 (C$_6$), 148.42 (C$_{14}$), 149.11 (C$_{15}$), 149.39 (C$_7$), and 169.96 (C$_{20}$). ESI$^+$ MS (m/z): 444.2 [M$^+$].

Example 10

This example describes the preparation of a mixture of the cis and trans isomers of (1R)-1-[(3,4-dimethoxyphenyl)methyl]-1,2,3,4-tetrahydro-6,7-dimethoxy-2-methyl-2-benzyloxycarbonylethyl-isoquinolinium besylate.

(1R)-1-[(3,4-dimethoxyphenyl)methyl]-1,2,3,4-tetrahydro-6,7-dimethoxy-2-benzyloxycarbonylethyl-isoquinoline oxalate (14.5 g, 0.0244 moles), prepared as detailed in example 4, was dissolved in water (100 ml) and 20% aqueous sodium hydroxide solution was added to produce a pH in the range of 9-10. Dichloromethane (70 ml) was added and the mixture was stirred for 15 minutes at ambient temperature. The upper organic layer was separated and the aqueous layer was extracted two times with dichloromethane (2×70 ml). The combined organic layers were washed with 10% sodium chloride solution. The organic layer was dried over magnesium sulfate and evaporated under reduced pressure to afford a residual oil. Dichloromethane (15 ml), methyl besylate (7.6 g, 0.0442 moles) and 0.5 ml of DMSO were added and the mixture was stirred at 10°-15° C. for 3 days. According to the HPLC analysis of the reaction mixture, it contained 78.6% of cis and 21.4% of trans isomers of (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate. Dichloromethane was evaporated from the reaction mixture under reduced pressure to obtain a residual oil. Diethyl ether (40 ml) was added to the residual oil and the emulsion was stirred at ambient temperature for 30 minutes. The solvent was decanted and the oil was dried to afford an oily mixture of 78% of the cis and 22% of the trans isomers of (1R)-1-[(3,4-dimethoxyphenyl)methyl]-1,2,3,4-tetrahydro-6,7-dimethoxy-2-methyl-2-benzyloxycarbonylethyl-isoquinolinium besylate (23.5 g).

Tetrahydrofuran (40 ml) was added to the residual oil and the mixture was heated to obtain a solution. The solution was cooled to ambient temperature and stirred for 1 hour. Subsequently, the mixture was cooled to −20° C. and kept at that temperature for 16 hours. The thus formed crystals were collected by filtration, washed with tetrahydrofuran and dried to afford a mixture of 76.6% of the cis and 23.4% of the trans isomers of (1R)-1-[(3,4-dimethoxyphenyl)methyl]-1,2,3,4-tetrahydro-6,7-dimethoxy-2-methyl-2-benzyloxycarbonyl-ethyl-isoquinolinium besylate (15.2 g, 92% yield).

Example 10A

This example describes the preparation of (1R-cis)-1-[(3,4-dimethoxyphenyl)-methyl]-1,2,3,4-tetrahydro-6,7-dimethoxy-2-methyl-2-benzyloxycarbonylethyl-isoquinolinium besylate by crystallization of isomeric mixture.

The mixture of 76.6% of the cis and 23.4% of the trans isomers of (1R)-1-[(3,4-dimethoxyphenyl)methyl]-1,2,3,4-tetrahydro-6,7-dimethoxy-2-methyl-2-benzyloxycarbonyl-ethyl-isoquinolinium besylate (3 g), prepared as detailed in example 10, was dissolved in dichloromethane (6 ml). Ethyl acetate (42 ml) was added to the solution. The mixture was kept at 5° C. for 48 hours to afford a suspension. The thus formed solid was collected by filtration, washed with ethyl acetate and dried to afford (1R-cis)-1-[(3,4-dimethoxyphenyl)-methyl]-1,2,3,4-tetrahydro-6,7-dimethoxy-2-methyl-2-benzyloxycarbonylethyl-isoquinolinium besylate, 1.7 g, (57% yield or 74% yield from the cis isomer), HPLC purity 98.65%, containing 1.35% of the trans isomer, m.p. 101.0°-103.5° C., $[\alpha]_D$ −41.4° (c=1.00, $CH_2Cl_2$).

The characteristic X-ray diffraction peaks are at the following peak positions (2θ): 6.3, 11.5, 13.0, 13.3, 13.7, 15.9, 16.7, 18.9, 19.4, 20.0, 20.3, 21.3, 22.6, 23.1, 24.0, 24.7.

Figure 6:
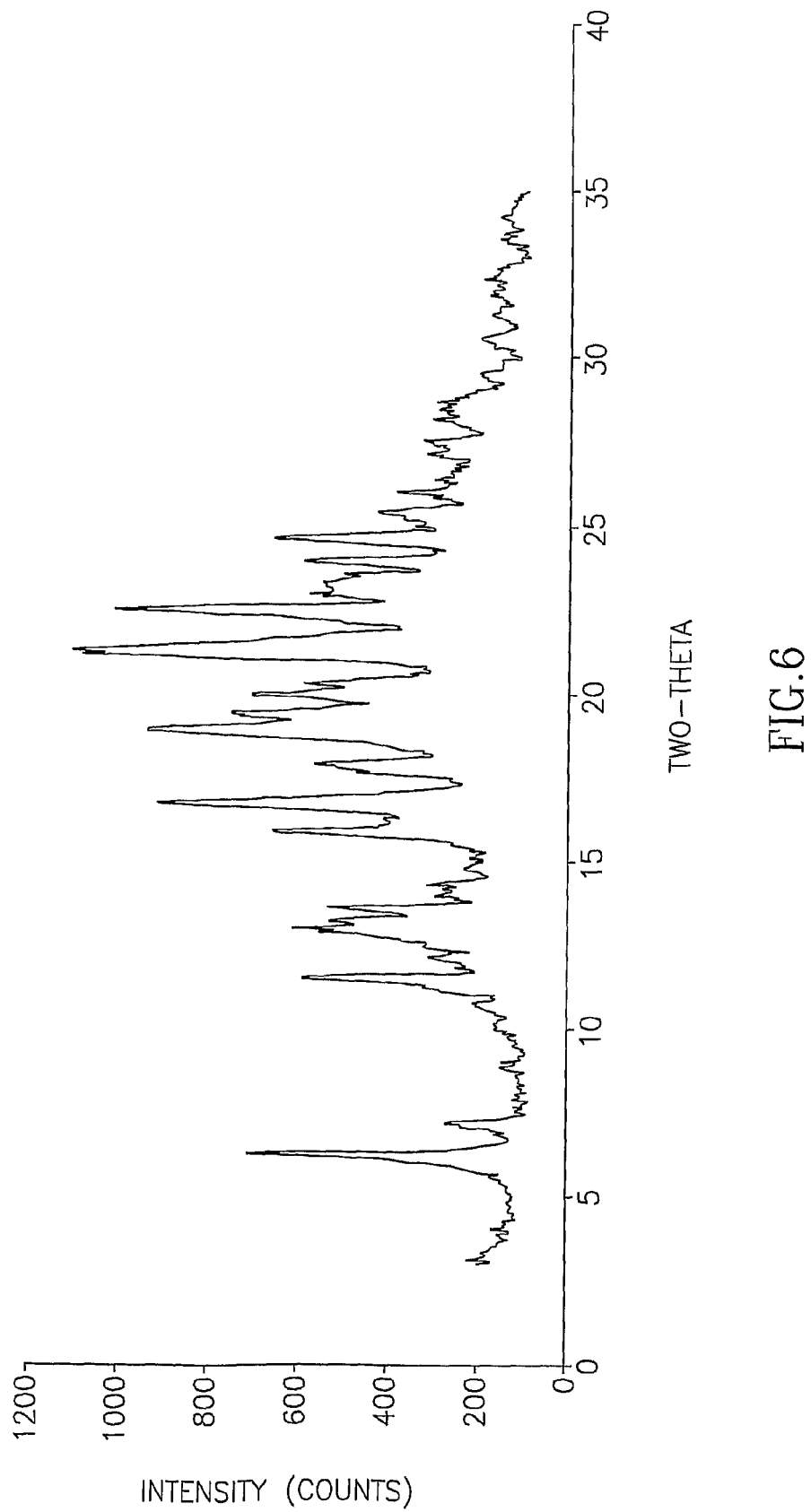
FIG. 6 illustrates the X-ray diffraction pattern for (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate.

FIG. 6 depicts the X-ray powder diffraction pattern.

The characteristic infrared absorption bands are at 3450.55, 2956.79, 2833.35, 1737.81, 1612.44, 1517.93, 1465.86, 1386.78, 1330.84, 1265.27, 1193.90, 1122.54, 1018.38, 852.51, 804.29, 725.21, 696.28, 613.35, 561.27 $cm^{-1}$.

Figure 13:
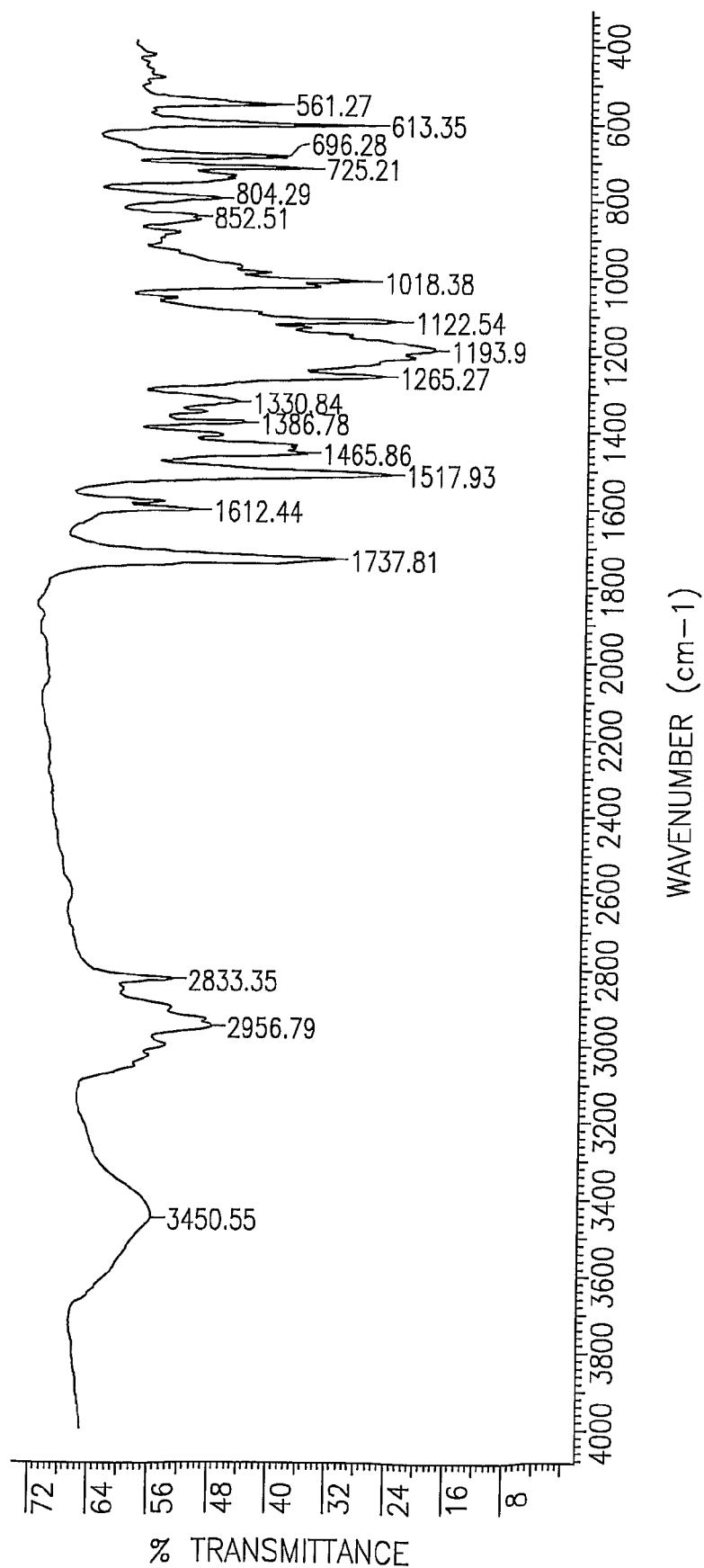
FIG. 13 illustrates the infrared spectrum for (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate.

FIG. 13 depicts the infrared spectrum.

Example 11

This example describes the preparation (1R-cis)-1-[(3,4-dimethoxyphenyl)-methyl]-1,2,3,4-tetrahydro-6,7-dimethoxy-2-methyl-2-benzyloxycarbonylethyl-isoquinolinium besylate.

(1R)-1-[(3,4-dimethoxyphenyl)methyl]-1,2,3,4-tetrahydro-6,7-dimethoxy-2-benzyloxycarbonylethylisoquinoline oxalate (24 g, 0.040 moles), prepared as detailed in example 4A, was dissolved in water (100 ml) and 50% aqueous sodium hydroxide solution was added to produce a pH in the range of 9-10. Dichloromethane (200 ml) was added and the mixture was stirred for 15 minutes at ambient temperature. The upper organic layer was separated. The aqueous layer was extracted with dichloromethane (200 ml). The combined organic layer was dried over magnesium sulfate. The organic layer was evaporated under reduced pressure to afford a residual oil. A solution of methyl benzenesulfonate (34.4 g, 0.200 moles) in dichloromethane (10 ml) was added and the mixture was stirred at ambient temperature for 3 days. According to the HPLC analysis, the reaction mixture contained 70% of cis and 20% of trans isomers of (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate. In addition, there remained 2.5% of the starting material (1R)-1-[(3,4-dimethoxyphenyl)methyl]-1,2,3,4-tetrahydro-6,7-dimethoxy-2-benzyloxycarbonylethylisoquinoline.

Dichloromethane was evaporated from the reaction mixture under reduced pressure to obtain a residual oil. The oil was dissolved in tetrahydrofuran (80 ml) and the mixture was cooled to 5° C. The mixture was seeded and stirred at 5° C. for 2 hours after which time a suspension had formed. The thus formed crystals were collected by filtration, washed with tetrahydrofuran and dried at ambient temperature under vacuum to afford (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate, 10 g, (47% yield), HPLC purity 97.5% with 0.6% of the trans isomer.

The same reaction was performed in the presence of DMSO (5 drops) using less methyl benzenesulfonate (15.8 g, 0.092 moles). The reaction was completed after 5 days to afford the same ratio of cis and trans isomers (70:20).

Example 12

This example describes the preparation of (1R-cis)-1-[(3,4-dimethoxyphenyl)-methyl]-1,2,3,4-tetrahydro-6,7-dimethoxy-2-methyl-2-benzyloxycarbonylethyl-isoquinolinium besylate.

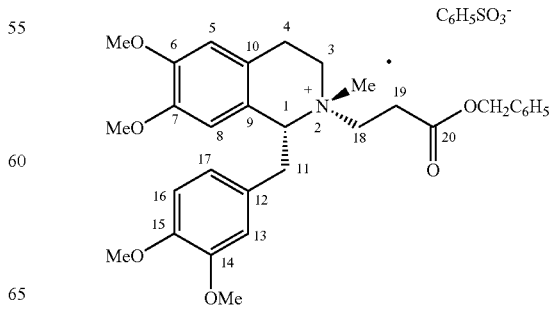

(1R)-1-[(3,4-dimethoxyphenyl)methyl]-1,2,3,4-tetrahydro-6,7-dimethoxy-2-benzyloxycarbonylethyl-isoquinoline oxalate (10.0 g, 0.0168 moles), prepared as detailed in example 4, was dissolved in water (50 ml) and 20% aqueous sodium hydroxide solution was added to produce a pH in the range of 9-10. Dichloromethane (100 ml) was added and the mixture was stirred for 15 minutes at ambient temperature. The upper organic layer was separated and the aqueous layer was extracted two times with dichloromethane (2×100 ml). The combined organic layer was washed with 10% sodium chloride solution. The organic layer was dried over magnesium sulfate and evaporated under reduced pressure to afford a residual oil. Dichloromethane (10 ml), methyl besylate (7.3 g, 0.0532 moles) and 0.5 ml of DMSO were added and the mixture was stirred at 10°-15° C. for 2 days. According to the HPLC analysis of the reaction mixture it contained 69.2% of the cis isomer and 19.8 of the trans isomer of (1R)-1-[(3,4-dimethoxyphenyl)methyl]-1,2,3,4-tetrahydro-6,7-dimethoxy-2-methyl-2-benzyloxycarbonylethyl-isoquinolinium besylate. The reaction mixture was washed three times with 10% sodium chloride solution (3×20) and then dried over magnesium sulfate. The dichloromethane was evaporated under reduced pressure to afford an oil consisting of a mixture of the cis and trans isomers of (1R)-1-[(3,4-dimethoxyphenyl)-methyl]-1,2,3,4-tetrahydro-6,7-dimethoxy-2-methyl-2-benzyloxycarbonylethyl-isoquinolinium besylate.

Tetrahydrofuran (40 ml) was added to the residual oil to obtain a solution. The solution was kept at 5° C. overnight. The solid was collected by filtration, washed with tetrahydrofuran (5 ml) and dried to afford (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate, 5.3 g, (46% yield or 68% yield from the cis isomer), HPLC purity 98.73% with 1.14% of the trans isomer, m.p. 102.0°-104.5° C., $[\alpha]_D$ −41.4° (c=1.00, $CH_2Cl_2$).

$^1H$ NMR ($CDCl_3$): δ=2.78-2.93 (m, 2H; $H_4$ and $H_{11}$), 3.01-3.07 (m, 1H) 3.11 (s, 3H, NMe), 3.24-3.31 (m, 2H), 3.37 (s, 3H, $OCH_3$), 3.48-3.53 (m, 2H), 3.62 (s, 3H, $OCH_3$), 3.71-3.75 (m, 1H), 3.77 (s, 3H, $OCH_3$), 3.78 (s, 3H, $OCH_3$), 3.93-4.03 (m, 1H), 4.14-4.22 (m, 1H), 4.96 (dd, 1H, $H_1$), 5.08 (s, 2H, $CH_2Ph$), 5.94 (s, 1H, $H_8$), 6.38-6.62 (m, 4H; $H_5$, $H_{13}$, $H_{16}$ and $H_{17}$), 7.17-7.25 (m, 3H, besylate), 7.27-7.32 (m, 5H, Ph), and 7.80-7.83 (m, 2H, besylate), $^{13}C$ NMR ($CDCl_3$): δ=23.25 ($C_4$), 27.70 ($C_{19}$), 37.58 ($C_{11}$), 46.54 ($NCH_3$), 53.53 ($C_3$), 55.58 ($OCH_3$), 55.84 ($OCH_3$), 55.89 ($OCH_3$), 55.92 ($OCH_3$), 58.50 ($C_{18}$), 67.21 ($CH_2Ph$), 70.74 ($C_1$), 110.49 ($C_5$), 111.09 ($C_{16}$), 111.80 ($C_8$), 113.23 ($C_{13}$), 120.52 ($C_{10}$), 121.64 ($C_9$), 122.45 ($C_{17}$), 125.83 (CH, Ph), 126.94 ($C_{12}$), 128.01, 128.37, 128.59 and 129.27 (CH, Ph), 135.27 (C, Ph), 146.71 (C, besylate), 147.12 ($C_6$), 148.20 ($C_{14}$), 148.94 ($C_{15}$), 149.14 ($C_7$), and 169.88 ($C_{20}$), ESI$^+$ MS (m/z): 520.4 [M$^+$].

Example 13

This example describes the preparation of a (1R-cis)-1-[(3,4-dimethoxyphenyl)-methyl]-1,2,3,4-tetrahydro-6,7-dimethoxy-2-methyl-2-benzyloxycarbonylethyl-isoquinolinium besylate.

A mixture of 75% of the cis and 25% of the trans isomers of (1R)-1-[(3,4-dimethoxyphenyl)methyl]-1,2,3,4-tetrahydro-6,7-dimethoxy-2-methyl-2-benzyloxycarbonylethyl-isoquinolinium besylate (5 g) was dissolved in acetone (20 ml) at 50° C. The resulting solution was cooled to 10° C. and kept at that temperature for 16 hours. The solid was collected by filtration, washed with acetone and dried at ambient temperature under reduced pressure to afford 0.54 g of (1R-trans)-1-[(3,4-dimethoxyphenyl)methyl]-1,2,3,4-tetrahydro-6,7-dimethoxy-2-methyl-2-benzyloxy-carbonylethyl-isoquinolinium besylate. According to the HPLC analysis, the product had purity of 90% and contained 8% of the cis isomer. The product was crystallized from acetone to afford the trans isomer having HPLC purity of 96.5% and m.p. 101.3°-102.5° C.

The combined mother liquor was evaporated to dryness under reduced pressure and the residue was dissolved in THF (20 ml) at 55°-60° C. The resulting solution was cooled to 10° C. and stirred for 16 hours. The thus obtained solid was separated by filtration, washed with THF and dried to afford (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate, 2.77 g, (55% yield or 74% yield from the cis isomer), HPLC purity 97.3% with 2.2% of the trans isomer; m.p. 80.4°-81.8° C.

Example 14

This example describes the preparation of (1R-cis)-1-[(3,4-dimethoxyphenyl)-methyl]-1,2,3,4-tetrahydro-6,7-dimethoxy-2-methyl-2-tert-butoxycarbonylethyl-isoquinolinium besylate.

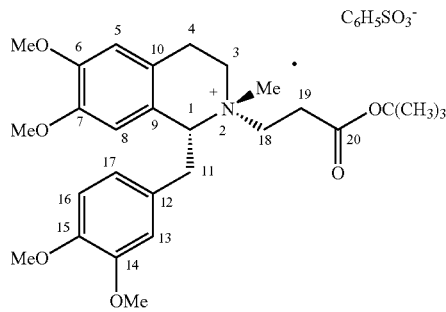

(1R)-1-[(3,4-dimethoxyphenyl)methyl]-1,2,3,4-tetrahydro-6,7-dimethoxy-2-tert-butoxycarbonylethyl-isoquinoline oxalate (20.0 g, 0.0356 moles) was dissolved in water (200 ml) and 25% aqueous sodium hydroxide solution was added to produce a pH in the range of 9-10. Toluene (100 ml) was added and the mixture was stirred for 15 minutes at ambient temperature. The upper organic layer was separated and the aqueous layer was extracted two times with toluene (2×100 ml). The combined organic layer was washed with 10% sodium chloride solution. The organic layer was dried over magnesium sulfate and evaporated under reduced pressure to afford crystals. Acetonitrile (10 ml) and methyl besylate (12.32 g, 0.0716 moles) were added to the crystals and the mixture was stirred at 30° C. for 20 hours. According to an HPLC analysis of the reaction mixture it contained 78.9% of cis and 21.1% of trans isomers of (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate. Dichloromethane (30 ml) was added to the reaction mixture under stirring to obtain a solution. Diethyl ether (40 ml) was then added to the solution and the mixture was stirred at ambient temperature overnight. The thus formed crystals were collected by filtration, washed with a diethyl ether:dichloromethane (4:3) mixture and dried to afford crude (1R-trans)-1-[(3,4-dimethoxyphenyl)methyl]-1,2,3,4-tetrahydro-6,7-dimethoxy-2-methyl-2-tert-butoxycarbonylethyl-isoquinolinium besylate, 3.0 g, HPLC purity: 95.35% with 0.52% of cis-isomer.

The solvents in the filtrate, obtained in the above example, were evaporated under reduced pressure. Ethyl acetate (30 ml) and diethyl ether (80 ml) were added to the thus formed residue and the mixture was stirred at ambient temperature for 2 hours to afford a suspension. The thus formed solid was collected by filtration, washed with an ethyl acetate:diethyl ether (3:8) mixture and dried to afford crude (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate, 12 g, HPLC purity: 94.7% with 3.25% of trans-isomer. The crude compound was dissolved in dichloromethane (25 ml) and ethyl acetate (75 ml) was added to the solution. The mixture was kept at ambient temperature overnight to obtain crystals, which were collected by filtration, washed with ethyl acetate and dried to afford cis-isomer, 10.8 g, (53.2% yield or 67.4% yield from cis-isomer); HPLC purity: 99.0% with 0.56% of trans-isomer; m.p. 121.0-123.5° C.; $[\alpha]_D$ −36.9° (c=1.00, $CH_2Cl_2$).

$^1$H NMR ($CDCl_3$): δ=1.44 (s, 9H, t-butyl), 2.83-3.23 (m, 4H, $H_4$, $H_{11}$, and $H_{19}$), 3.12 (s, 3H, NMe), 3.41 (s, 3H, $OCH_3$), 3.48-3.64 (m, 2H, $H_4$ and $H_{19}$), 3.66 (s, 3H, $OCH_3$), 3.77-3.87 (m, 1H, $H_3$), 3.80 (s, 3H, $OCH_3$), 3.81 (s, 3H, $OCH_3$), 3.92 (m, 2H, $H_3$ and $H_{18}$), 4.10 (m, 1H, $H_{18}$), 4.95 (m, 1H, $H_1$), 5.98 (s, 1H, $H_8$), 6.45 (d, 1H, $H_{17}$), 6.49 (s, 1H, $H_{13}$), 6.57 (s, 1H, $H_5$), 6.65 (d, 1H, $H_{16}$), 7.28-7.34 (m, 3H, besylate), and 7.83-7.90 (m, 2H, besylate). $^{13}$C NMR ($CDCl_3$): δ=23.20 ($C_4$), 27.89 (C—$CH_3$), 28.56 ($C_{19}$), 37.49 ($C_{11}$), 46.54 ($NCH_3$), 53.50 ($C_3$), $\overline{55.53}$ ($OCH_3$), 55.76 ($OCH_3$), 55.82 ($\overline{OCH}_3$), 55.85 ($OCH_3$), 58.63 ($\overline{C}_{18}$), 70.67 ($C_1$), $\overline{82.32}$ ($CMe_3$), $\overline{1}10.44$ ($C_5$), $\overline{1}11.02$ ($C_{16}$), 111.72 ($C_8$), 113.17 ($\overline{C}_{13}$), 120.49 ($C_{10}$), 121.53 ($C_9$), 122.31 ($C_{17}$), 125.77 (CH, besylate), 126.84 ($C_{12}$), 127.91 and 129.20 (CH, besy$\overline{late}$), 146.58 (C, besylate), 147.08 ($C_6$), 148.15 ($C_{14}$), 148.87 ($C_{15}$), 149.10 ($C_7$), and 168.88 ($C_{20}$), ESI$^+$ MS (m/z): 486.2 [M$^+$].

The characteristic X-ray diffraction peaks are at the following peak positions (2θ): 7.2, 10.6, 11.8, 14.2, 17.1, 18.6, 21.0, 21.5, 23.6, 25.3, 28.2.

Figure 7:
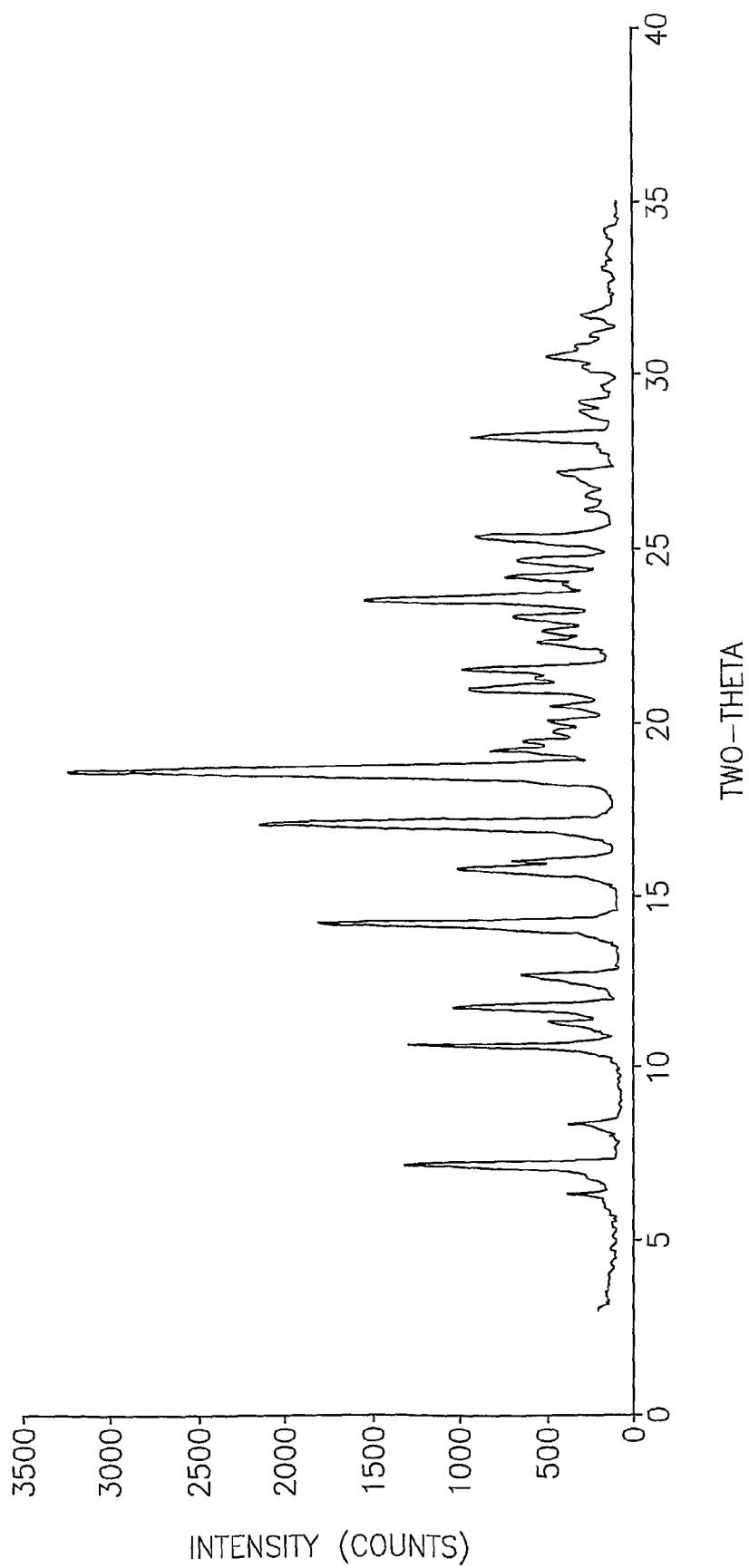
FIG. 7 illustrates the X-ray diffraction pattern for (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate.

FIG. 7 depicts the X-ray powder diffraction pattern.

The characteristic infrared absorption bands are at 3429.33, 2997.29, 2956.79, 2835.28, 1728.17, 1610.51, 1597.01, 1517.93, 1444.64, 1367.49, 1334.70, 1265.27, 1193.90, 1157.26, 1120.61, 1016.46, 896.87, 848.65, 759.93, 723.28, 696.28, 611.42, 561.27, 433.97 cm$^{-1}$.

Figure 14:
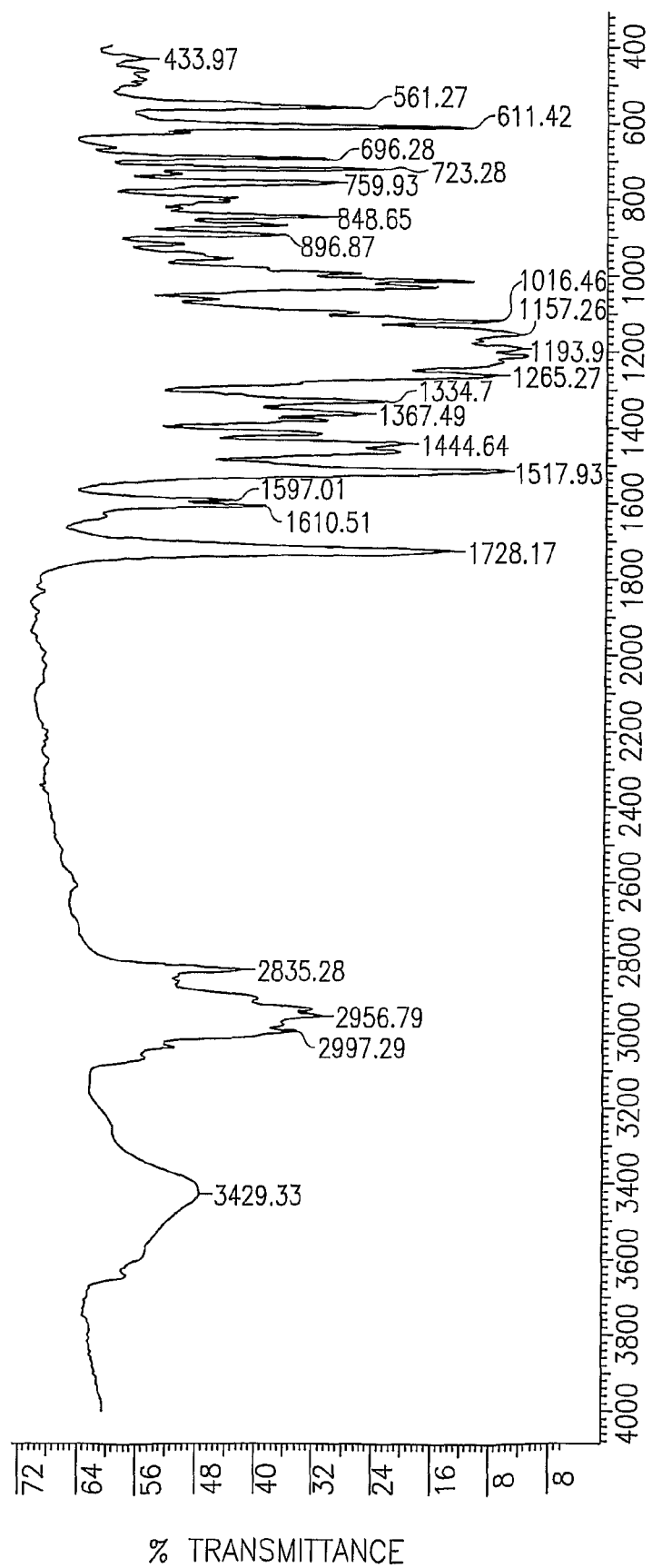
FIG. 14 illustrates the infrared spectrum for (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate.

FIG. 14 depicts the Infrared spectrum.

The following examples illustrate the preparation of quaternary ammonium salts of carboxylic acids from the quaternary ammonium salts of esters and amides prepared according to examples 6-14.

Example 15

This example describes the preparation of a mixture of the cis and trans isomers of (1R)-1-[(3,4-dimethoxyphenyl)methyl]-1,2,3,4-tetrahydro-6,7-dimethoxy-2-methyl-2-carboxyethyl-isoquinolinium tetrafluoroborate.

(1R)-1-[(3,4-dimethoxyphenyl)methyl]-1,2,3,4-tetrahydro-6,7-dimethoxy-2-tert-butoxycarbonylethyl-isoquinoline (1.6 g, 0.0034 moles) was dissolved in dichloromethane (20 ml) and the solution was cooled to 0° C. Trimethyloxonium tetrafluoroborate (1.1 g, 0.0074 moles) was added to the solution in 3 portions during 30 minutes. The mixture was stirred at 0° C. for 1 hour and kept at ambient temperature for 16 hours. The mixture was analyzed by HPLC to afford a mixture of 74.1% of the cis and 25.9% of the trans isomers of (1R)-1-[(3,4-dimethoxyphenyl)-methyl]-1,2,3,4-tetrahydro-6,7-dimethoxy-2-methyl-2-carboxyethyl-isoquinolinium tetrafluoroborate. The mixture was filtered and diethyl ether (40 ml) was added to the filtrate and the mixture was stirred at ambient temperature for 30 minutes. The solvent was decanted from the thus precipitated oily residue. Ethyl acetate was added to the oily residue (30 ml) and the mixture was stirred at ambient temperature for 1 hour to afford a suspension. The thus formed solid was collected by filtration, washed with ethyl acetate and dried to afford a mixture of 83.8% of the cis and 16.9% of the trans isomers of (1R)-1-[(3,4-dimethoxy-phenyl)methyl]-1,2,3,4-tetrahydro-6,7-dimethoxy-2-methyl-2-carboxyethyl-isoquinolinium tetrafluoroborate (1.75 g; 92% yield).

Example 15A

This example describes the isolation of (1R-cis)-1-[(3,4-dimethoxyphenyl)-methyl]-1,2,3,4-tetrahydro-6,7-dimethoxy-2-methyl-2-carboxylethyl-isoquinolinium tetrafluoroborate by slurrying the isomer mixture in dichloromethane.

A mixture of the cis and the trans isomers of (1R)-1-[(3,4-dimethoxyphenyl)-methyl]-1,2,3,4-tetrahydro-6,7-dimethoxy-2-methyl-2-carboxyethyl-isoquinolinium tetrafluoroborate (1.0 g), prepared as detailed in example 15, was admixed with dichloromethane (30 ml) and heated to reflux for 1 hour to afford a suspension. The mixture was cooled to ambient temperature. The thus formed solid was collected by filtration, washed with dichloromethane and dried at 40° C. to afford (1R-cis)-1-[(3,4-dimethoxyphenyl)methyl]-1,2,3,4-tetrahydro-6,7-dimethoxy-2-methyl-2-carboxyethyl-isoquinolinium tetrafluoroborate, 0.5 g, (50% yield or 60% yield from the cis isomer), HPLC purity 99.2% with 0.8% of the trans isomer, m.p. 187°-190° C. (dec.), $[\alpha]_D$ −83.6° (c=1.02, DMSO).

Example 15B

This example describes the preparation of (1R-cis)-1-[(3,4-dimethoxyphenyl)-methyl]-1,2,3,4-tetrahydro-6,7-dimethoxy-2-methyl-2-carboxyethyl-isoquinolinium tetrafluoroborate.

Water (2 ml) and 48% aqueous tetrafluoroboric acid solution (1 ml) were admixed with (1R-cis)-1-[(3,4-dimethoxyphenyl)methyl]-1,2,3,4-tetrahydro-6,7-dimethoxy-2-methyl-2-carboxyethyl-isoquinolinium besylate, having HPLC purity of 99.0% (1.0 g), and the mixture was stirred at 60° C. for 15 minutes to afford a suspension. The suspension was stirred at ambient temperature for 1 hour and then it was filtered. The thus obtained solid was washed with water (1 ml), then with acetonitrile (3 ml) and dried at 40° C. under reduced pressure to afford (1R-cis)-1-[(3,4-dimethoxyphenyl)methyl]-1,2,3,4-tetrahydro-6,7-dimethoxy-2-methyl-2-carboxyethyl-isoquinolinium tetrafluoroborate, 0.8 g, (91% yield), HPLC purity: 99.5%.

Example 16

This example describes the preparation of (1R-cis)-1-[(3,4-dimethoxyphenyl)-methyl]-1,2,3,4-tetrahydro-6,7-dimethoxy-2-methyl-2-carboxyethyl-isoquinolinium iodide.

(a) hydrolysis with trifluoroacetic acid (TFA)

(1R-cis)-1-[(3,4-dimethoxyphenyl)methyl]-1,2,3,4-tetrahydro-6,7-dimethoxy-2-methyl-2-tert-butoxycarbonylethyl-isoquinolinium iodide (0.4 g, HPLC purity: 97.6% with 2.4% of the trans isomer) was admixed with dichloromethane (15 ml) and stirred to obtain a solution. TFA (5 ml) was added and the reaction mixture was stirred at ambient temperature for 20 minutes. Reaction completion was checked by HPLC.

The reaction mixture was concentrated to one-third of its volume. The residue was added dropwise to diethyl ether (50 ml) to afford a suspension. The thus obtained solid was collected by filtration, washed with diethyl ether and dried under reduced pressure to obtain crude (1R-cis)-1-[(3,4-dimethoxyphenyl)-methyl]-1,2,3,4-tetrahydro-6,7-dimethoxy-2-methyl-2-carboxyethyl-isoquinolinium iodide, 0.35 g, (96% yield), HPLC purity: 96.5%, containing 2.2% of the trans isomer.

(b) hydrolysis with iodotrimethylsilane (1R-cis)-1-[(3,4-dimethoxyphenyl)methyl]-1,2,3,4-tetrahydro-6,7-dimethoxy-2-methyl-2-tert-butoxycarbonylethyl-isoquinolinium iodide (8.14 g, 0.0145 moles; HPLC purity: 97.0% with 3.0% of the trans isomer) was admixed with dichloromethane (70 ml) and stirred to obtain a solution. Iodotrimethylsilane (2.43 ml, 0.0171 moles) was added dropwise at ambient temperature. The reaction mixture was stirred at ambient temperature for 15 minutes. Water (20 ml) was added to the mixture. The aqueous layer was separated and washed with three portions of dichloromethane (3×20 ml). The dichloromethane extracts were combined and dried over magnesium sulfate. The dichloromethane layer was evaporated under reduced pressure to afford crude (1R-cis)-1-[(3,4-dimethoxyphenyl)methyl]-1,2,3,4-tetrahydro-6,7-dimethoxy-2-methyl-2-carboxyethyl-isoquinolinium iodide, 8.2 g, (97% yield); HPLC purity: 97.0% with 3.0% of the trans isomer. The crude product was combined with dichloromethane (80 ml) and the mixture was heated at reflux for 4 hours to afford a suspension. The suspension was cooled to ambient temperature. The thus formed white solid was collected by filtration, washed with dichloromethane and dried at 40° C. to afford (1R-cis)-1-[(3,4-dimethoxyphenyl)methyl]-1,2,3,4-tetrahydro-6,7-dimethoxy-2-methyl-2-carboxyethyl-isoquinolinium iodide, 7.85 g, (96% yield), 99.5% HPLC purity with 0.5% of the trans isomer, m.p. 175°-177° C., $[\alpha]_D$ −69.7° (c=1.0, DMSO:CH$_2$Cl$_2$ in a ratio of 33:1).

Example 17

This example describes the preparation of (1R-cis)-1-[(3,4-dimethoxyphenyl)-methyl]-1,2,3,4-tetrahydro-6,7-dimethoxy-2-methyl-2-carboxyethyl)-isoquinolinium besylate by hydrogenation of (1R-cis)-1-[(3,4-dimethoxyphenyl)-methyl]-1,2,3,4-tetrahydro-6,7-dimethoxy-2-methyl-2-benzyloxycarbonylethyl-isoquinolinium besylate.

(1R-cis)-1-[(3,4-dimethoxyphenyl)methyl]-1,2,3,4-tetrahydro-6,7-dimethoxy-2-methyl-2-benzyloxycarbonylethyl-isoquinolinium besylate (2.7 g, 0.00352 moles), (HPLC purity 97.3%, containing 2.2% of the trans isomer) was dissolved in anhydrous methanol (16 ml). To the solution was added 5% Pd/C (0.2 g) and the reaction mixture was hydrogenated at 10° C. for 2 hours. The mixture was filtered to remove the catalyst and the filtrate was evaporated to afford (1R-cis)-1-[(3,4-dimethoxyphenyl)methyl]-1,2,3,4-tetrahydro-6,7-dimethoxy-2-methyl-2-carboxyethyl-isoquinolinium besylate, 2.16 g, (yield 92%), HPLC purity 97.0% with 1.7% of the trans isomer, m.p. 51.2°-52.3° C.

Example 18

This example describes the preparation of (1R-cis)-1-[(3,4-dimethoxyphenyl)-methyl]-1,2,3,4-tetrahydro-6,7-dimethoxy-2-methyl-2-carboxyethyl-isoquinolinium besylate by hydrolysis of (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate.

(a) hydrolysis with trifluoroacetic acid (TFA)

(1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate (1 g, HPLC purity 99.0%) was added to TFA (2.5 ml), cooled to 0-5° C., and the reaction mixture was stirred for 20 minutes. Then, TFA was removed from the reaction mixture to dryness at 30-40° C. under reduced pressure to afford (1R-cis)-1-[(3,4-dimethoxyphenyl)methyl]-1,2,3,4-tetrahydro-6,7-dimethoxy-2-methyl-2-carboxyethyl-isoquinolinium besylate, 0.91 g, (100% yield); HPLC purity: 97.1% with 0.56% of trans-isomer.

(b) with 1 equivalent of TFA in water

A mixture of (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate (1.3 g, HPLC purity 99.0%), water (5 ml) and TFA (0.18 ml, 1 eq.) was stirred at 35-40° C. for 6 hours. Then, toluene was added and water and TFA were removed from the reaction mixture to dryness by azeotropic distillation to afford (1R-cis)-1-[(3,4-dimethoxyphenyl)methyl]-1,2,3,4-tetrahydro-6,7-dimethoxy-2-methyl-2-carboxylethyl-isoquinolinium besylate, 1.18 g, (100% yield); HPLC purity: 97.0% with 0.56% of trans-isomer.

(c) with 0.2 equivalents of benzenesulfonic acid in water

A mixture of (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate (1.43 g, HPLC purity 99.0%), water (5 ml) and benzenesulfonic acid (72 mg, 0.2 eq.) was stirred at 35-40° C. for 6 hours. Then, toluene was added and water and TFA were removed from the reaction mixture to dryness by azeotropic distillation to afford (1R-cis)-1-[(3,4-dimethoxyphenyl)methyl]-1,2,3,4-tetrahydro-6,7-dimethoxy-2-methyl-2-carboxyethyl-isoquinolinium besylate (1.38 g, 100% yield; HPLC purity: 96.44% with 0.56% of trans-isomer).

(d) with Amberlyst®15 hydrogen form in water

A mixture of (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate (1.34 g, HPLC purity 99.0%), water (6.5 ml) and Amberlyst®15 hydrogen form (0.33 g) was stirred at 35-40° C. for 6 hours. The Amberlyst®15 hydrogen form was collected by filtration. Then, toluene was added and water was removed from the reaction mixture to dryness by azeotropic distillation to afford (1R-cis)-1-[(3,4-dimethoxyphenyl)-methyl]-1,2,3,4-tetrahydro-6,7-dimethoxy-2-methyl-2-carboxyethyl-isoquinolinium besylate as colorless foam 1.20 g, (98.4% yield); HPLC purity: 98.45% with 0.56% of trans-isomer.

Example 19

This example describes the preparation of crude cisatracurium besylate.

(1R-cis)-1-[(3,4-dimethoxyphenyl)methyl]-1,2,3,4-tetrahydro-6,7-dimethoxy-2-methyl-2-carboxyethyl-isoquinolinium besylate (0.53 g, 0.9018 mmoles) was dissolved in anhydrous dichloromethane (10 ml). The solution was cooled to 0° C. and oxalyl chloride (0.086 ml, 0.9920 mmoles) was added dropwise at 0° C. The reaction mixture was allowed to reach ambient temperature and stirred for 2 hours. Subsequently, the temperature was reduced to at 0° C. and 1,5-pentanediol (0.050 ml, 0.4734 mmoles) was added dropwise at that temperature. The reaction mixture was allowed to reach ambient temperature and stirred for 4 hours. After concentrating the solution under reduced pressure at ambient temperature, the residue was dissolved in a mixture of water (10 ml) and toluene (20 ml) to afford a two phase system. The layers were separated and the aqueous layer was washed first with a mixture of ethyl acetate and n-heptane (5:1 v/v, 20 ml)

followed by toluene (20 ml). To the aqueous layer was added dichloromethane (50 ml) to afford a two phase system. The dichloromethane layer, containing the product, was dried and evaporated under reduced pressure to afford crude cisatracurium besylate (0.260 g, 23% yield).

Example 20

This example describes the preparation of crude cisatracurium iodide.

(1R-cis)-1-[(3,4-dimethoxyphenyl)methyl]-1,2,3,4-tetrahydro-6,7-dimethoxy-2-methyl-2-carboxyethyl-isoquinolinium iodide (0.50 g, 0.917 mmoles) was dissolved in anhydrous dichloromethane (15 ml). The resulting suspension was cooled to 0° C. and thionyl chloride (0.10 ml, 1.376 mmoles) was added in portions. The reaction mixture was allowed to reach ambient temperature stirred at that temperature for 2 hours. 1,5-pentanediol (0.05 ml, 0.481 mmoles) was added dropwise at 0° C. and the reaction mixture was allowed to reach ambient temperature and reaction mixture was stirred at that temperature for 14 hours. After concentrating the reaction mixture under reduced pressure at room temperature, the crude cisatracurium iodide was obtained as a semi-solid oil, 0.752 g, (69% yield); HPLC purity: 80%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound having the structural formula (VIII)

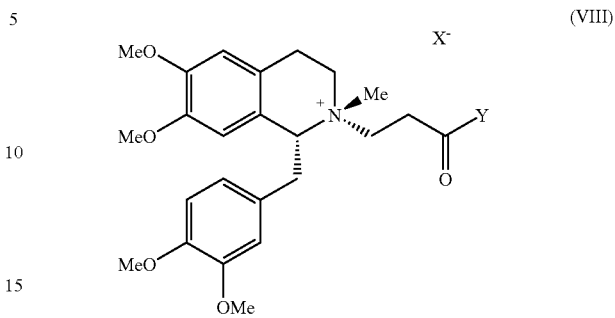

wherein $X^-$ is an anion selected from chloride, bromide, iodide, tetrafluoroborate, sulfate, hydrogensulfate, methanesulfonate, benzenesulfonate, p-toluenesulfonate, naphthalene-1-sulfonate, naphthalene-2-sulfonate, oxalate, and tartrate, and Y is $OR_1$ or $NR_2R_3$, $R_1$, $R_2$ and $R_3$ are the same or different and each is independently selected from hydrogen, alkyl, aryl, and heteroaryl with the proviso that Y is not OH.

2. The compound of claim 1 in substantially crystalline form, wherein $X^-$ is benzenesulfonate(besylate) or iodide.

3. The compound of claim 2, which is:
   (1R-cis)-1-[(3,4-dimethoxyphenyl)methyl]-1,2,3,4-tetrahydro-6,7-dimethoxy-2-methyl-2-tert-butoxycarbonylethyl-isoquinolinium iodide,
   (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate,
   (1R-cis)-1-[(3,4-dimethoxyphenyl)methyl]-1,2,3,4-tetrahydro-6,7-dimethoxy-2-methyl-2-aminocarbonylethyl-isoquinolinium iodide,
   (1R-cis)-1-[(3,4-dimethoxyphenyl)methyl]-1,2,3,4-tetrahydro-6,7-dimethoxy-2-methyl-2-methoxycarbonylethyl-isoquinolinium iodide, or
   (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate.

4. The compound of claim 3, which is a crystalline form of (1R-cis)-1-[(3,4-dimethoxyphenyl)methyl]-1,2,3,4-tetrahydro-6,7-dimethoxy-2-methyl-2-tert-butoxycarbonylethyl-isoquinolinium besylate characterized by an X-ray powder diffraction pattern exhibiting strong diffraction peaks at 7.2, 10.6, 11.8, 14.2, 15.8, 17.1, 18.6, 21.0, 23.6, 25.3 and 28.2±0.2 degrees 2θ.

5. The compound of claim 3, which is a crystalline form of (1R-cis)-1-[(3,4-dimethoxyphenyl)methyl]-1,2,3,4-tetrahydro-6,7-dimethoxy-2-methyl-2-aminocarbonylethyl-isoquinolinium iodide characterized by an X-ray powder diffraction pattern exhibiting strong diffraction peaks at 4.8, 17.8, 18.3, 21.1, 24.5 and 25.8±0.2 degrees 2θ.

6. The compound of claim 3, which is a crystalline form of (1R-cis)-1-[(3,4-dimethoxyphenyl)methyl]-1,2,3,4-tetrahydro-6,7-dimethoxy-2-methyl-2-benzyloxycarbonylethyl-isoquinolinium besylate characterized by an X-ray powder diffraction pattern exhibiting strong diffraction peaks at 6.3, 11.5, 13.0, 13.3, 13.7, 15.9, 16.7, 18.9, 19.4, 20.0, 20.3, 21.3, 22.6, 23.1, 24.0 and 24.7±0.2 degrees 2θ.

7. The compound of claim 3 having a purity greater than 98%.

8. The compound of claim 7 having a purity greater than 99%.

9. A compound having the structural formula (X)

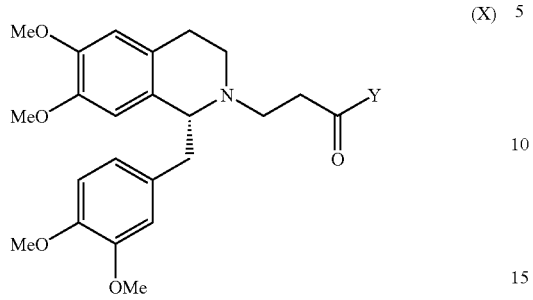

(X)

or an acid addition salt thereof, wherein Y is methoxy, tert-butoxy, benzyloxy, amino or tert-butylamino.

10. The compound of claim 9 in the form of an acid addition salt, in substantially crystalline form, which is:
- (1R)-1-[(3,4-dimethoxyphenyl)methyl]-1,2,3,4-tetrahydro-6,7-dimethoxy-2-tert-butoxycarbonylethyl-isoquinoline oxalate,
- (1R)-1-[(3,4-dimethoxyphenyl)methyl]-1,2,3,4-tetrahydro-6,7-dimethoxy-2-aminocarbonylethyl-isoquinoline oxalate,
- (1R)-1-[(3,4-dimethoxyphenyl)methyl]-1,2,3,4-tetrahydro-6,7-dimethoxy-2-methoxycarbonylethyl-isoquinolinium oxalate,
- (1R)-1-[(3,4-dimethoxyphenyl)methyl]-1,2,3,4-tetrahydro-6,7-dimethoxy-2-benzyloxycarbonylethyl-isoquinolinium oxalate, or
- (1R)-1-[(3,4-dimethoxyphenyl)methyl]-1,2,3,4-tetrahydro-6,7-dimethoxy-2-tert-butylaminocarbonylethyl-isoquinolinium oxalate.

11. The compound of claim 9, which is a crystalline form of (1R)-1-[(3,4-dimethoxyphenyl)methyl]-1,2,3,4-tetrahydro-6,7-dimethoxy-2-tert-butoxycarbonylethyl-isoquinolinium oxalate characterized by an X-ray powder diffraction pattern exhibiting strong diffraction peaks at 7.8, 11.3, 14.7, 16.7, 17.5, 19.3, 22.0, 23.1, 23.4 and 25.4±0.2 degrees 2θ.

12. The compound of claim 9, which is a crystalline form of (1R)-1-[(3,4-dimethoxyphenyl)methyl]-1,2,3,4-tetrahydro-6,7-dimethoxy-2-aminocarbonylethyl-isoquinolinium oxalate characterized by an X-ray powder diffraction pattern exhibiting strong diffraction peaks at 7.8, 10.2, 17.4, 21.5, 23.5, 25.5 and 27.1±0.2 degrees 2θ.

13. The compound of claim 9, which is a crystalline form of (1R)-1-[(3,4-dimethoxyphenyl)methyl]-1,2,3,4-tetrahydro-6,7-dimethoxy-2-benzyloxycarbonylethyl-isoquinolinium oxalate characterized by an X-ray powder diffraction pattern exhibiting strong diffraction peaks at 5.2, 7.8, 14.0, 17.3, 17.6 and 23.5±0.2 degrees 2θ.

14. The compound of claim 9, which is a crystalline form of (1R)-1-[(3,4-dimethoxyphenyl)methyl]-1,2,3,4-tetrahydro-6,7-dimethoxy-2-tert-butylaminocarbonylethyl-isoquinolinium oxalate characterized by an X-ray powder diffraction pattern exhibiting strong diffraction peaks at 5.4, 6.9, 12.6, 15.8, 17.8, 19.3, 26.2 and 26.8±0.2 degrees 2θ.

15. A crystalline compound of the formula:

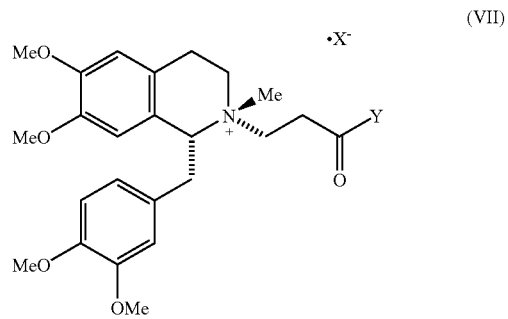

(VII)

wherein $X^-$ is an anion selected from chloride, bromide, iodide, methanesulfonate, benzenesulfonate, p-toluenesulfonate, naphthalene-1-sulfonate, naphthalene-2-sulfonate, tetrafluoroborate, oxalate, and tartarate.

16. The crystalline compound of claim 15, wherein $X^-$ is selected from benzenesulfonate, iodide and tetrafluoroborate.

17. A compound of the formula:

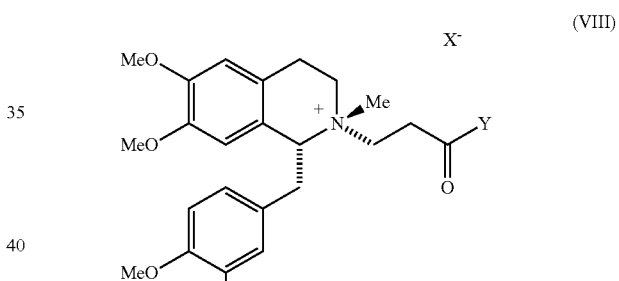

(VIII)

wherein $X^-$ is an anion, and Y is $OR_1$ or $NR_2R_3$, wherein $R_1$, $R_2$ and $R_3$ are the same or different and each is independently selected from hydrogen, alkyl, aryl, and heteroaryl with the proviso that Y is not OH.

18. A crystalline compound of the formula:

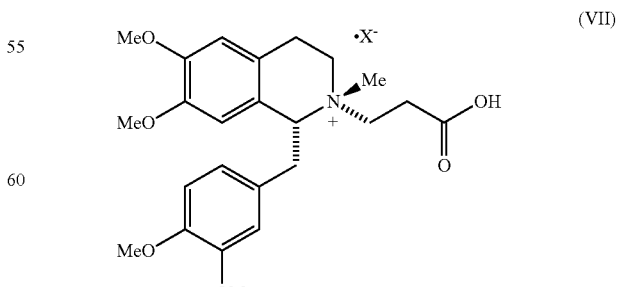

(VII)

wherein X− is an anion.

19. A method for preparing a cisatracurium salt, the method comprising converting a compound of the formula

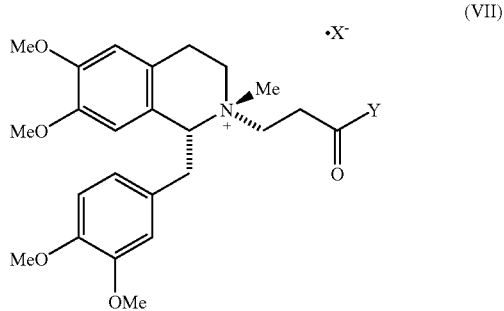

(VII)

wherein X– is an anion, into a cisatracurium salt by reacting the compound of formula (VII) or an activated derivative thereof with 1,5-pentanediol to produce the cisatracurium salt.

20. The method of claim 19, wherein the cisatracurium salt is cisatracurium besylate.

21. The method of claim 19, wherein X– is selected from chloride, bromide, iodide, tetrafluoroborate, sulfate, hydrogensulfate, methanesulfonate, benzenesulfonate, p-toluenesulfonate, naphthalene-1-sulfonate, naphthalene-2-sulfonate, oxalate, and tartarate.

22. The method of claim 19, wherein X– is benzenesulfonate.

* * * * *